(12) United States Patent
Vonesh et al.

(10) Patent No.: US 6,336,937 B1
(45) Date of Patent: Jan. 8, 2002

(54) MULTI-STAGE EXPANDABLE STENT-GRAFT

(75) Inventors: Michael J. Vonesh; Edward H. Cully; Gerald R. Martin; Steven R. Bruun; Dennis L. Salzmann, all of Flagstaff, AZ (US)

(73) Assignee: Gore Enterprise Holdings, Inc., Newark, DE (US)

( * ) Notice: Subject to any disclaimer, the term of this patent is extended or adjusted under 35 U.S.C. 154(b) by 0 days.

(21) Appl. No.: 09/207,944

(22) Filed: Dec. 9, 1998

(51) Int. Cl.$^7$ .................................................. A61F 2/06
(52) U.S. Cl. ...................................................... 623/1.13
(58) Field of Search ............................... 606/108, 198, 606/195, 191; 604/7, 8, 96; 623/14, 1.37, 1.44, 1.17, 1.12, 1.39, 1.22–1.23, 1.1, 1.11, 1.13, 1.14, 1.15, 1.16, 1.18, 1.19, 1.2, 1.21

(56) References Cited

U.S. PATENT DOCUMENTS

| | | | |
|---|---|---|---|
| 3,953,566 A | | 4/1976 | Gore ........................... 264/288 |
| 3,962,153 A | | 6/1976 | Gore ......................... 260/2.5 R |
| 4,096,227 A | | 6/1978 | Gore ........................... 264/210 R |
| 4,187,390 A | | 2/1980 | Gore ....................... 174/102 R |
| 4,813,925 A | * | 3/1989 | Anderson, Jr. et al. .......... 604/8 |
| 4,902,423 A | | 2/1990 | Bacino .................. 210/500.36 |
| 5,292,321 A | * | 3/1994 | Lee .............................. 606/198 |
| 5,443,497 A | * | 8/1995 | Venbrux ........................ 623/1 |
| 5,474,563 A | * | 12/1995 | Myler et al. ................. 606/195 |
| 5,628,786 A | | 5/1997 | Banas et al. .................... 623/1 |
| 5,669,924 A | * | 9/1997 | Shaknovich ................. 606/108 |
| 5,707,354 A | * | 1/1998 | Salmon et al. ................. 604/96 |
| 5,723,003 A | * | 3/1998 | Winston et al. ................. 623/1 |
| 5,747,128 A | | 5/1998 | Campbell et al. .......... 428/35.7 |
| 5,749,848 A | * | 5/1998 | Jang et al. ..................... 604/53 |
| 5,749,880 A | * | 5/1998 | Banas et al. ................. 606/198 |
| 5,776,161 A | * | 7/1998 | Globerman ..................... 623/1 |
| 5,843,158 A | * | 12/1998 | Lenker et al. .................. 623/1 |
| 5,851,210 A | * | 12/1998 | Torssian ..................... 606/108 |
| 5,911,725 A | * | 6/1999 | Boury ........................ 606/108 |
| 5,948,018 A | * | 9/1999 | Dereume et al. ............... 623/1 |
| 5,964,798 A | * | 10/1999 | Imram ........................... 623/1 |
| 6,120,535 A | * | 9/2000 | McDonald et al. ......... 623/1.39 |
| 6,176,875 B1 | * | 1/2001 | Lenker et al. ............. 623/1.49 |
| 6,264,684 B1 | * | 7/2001 | Banas et al. ............... 623/1.13 |

FOREIGN PATENT DOCUMENTS

| | | |
|---|---|---|
| WO | 96/19257 | 6/1996 |
| WO | 97/07751 | 3/1997 |
| WO | 97/17898 | 5/1997 |
| WO | 97/21403 | 6/1997 |
| WO | 98/00090 | 1/1998 |
| WO | 98/32412 | 7/1998 |

\* cited by examiner

*Primary Examiner*—David O. Reip
*Assistant Examiner*—Vy Q. Bui
(74) *Attorney, Agent, or Firm*—David J Johns

(57) ABSTRACT

An improved device for use in a conduit, such as a blood vessel, is provided. The device uniquely combines desirable properties from two distinct previous devices. The device of the present invention assumes and is constrained to a first diametrical dimension for insertion into the conduit. Once inserted and properly positioned in the conduit the device expands to a second diametrical dimension within the conduit when the constraint is removed. The device can then be dilated to one or more enlarged third diametrical dimensions by using a balloon catheter or similar device. The result is a device that provides desirable properties of both self-expanding stents and balloon-expandable endoprostheses. The device can be employed in a variety of applications.

41 Claims, 15 Drawing Sheets

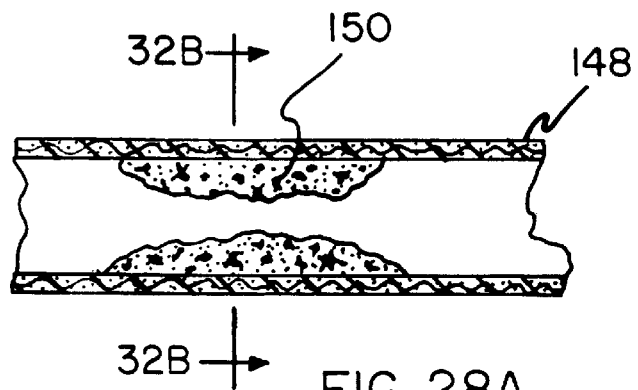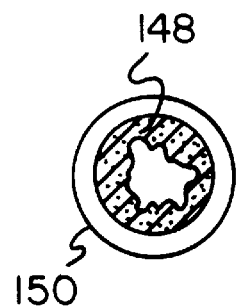
FIG. 28A  FIG. 28B
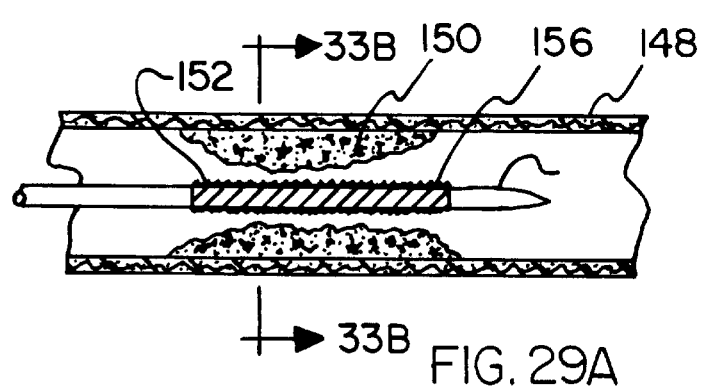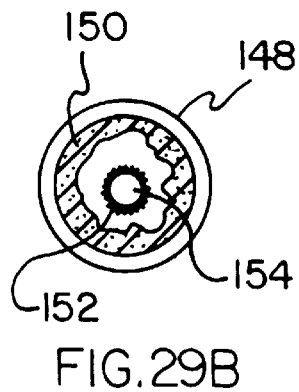
FIG. 29A  FIG. 29B
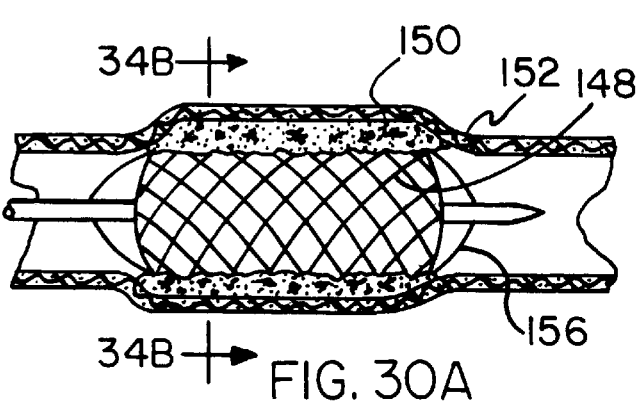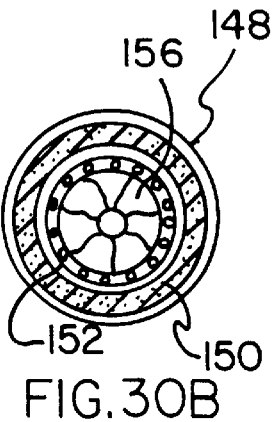
FIG. 30A  FIG. 30B
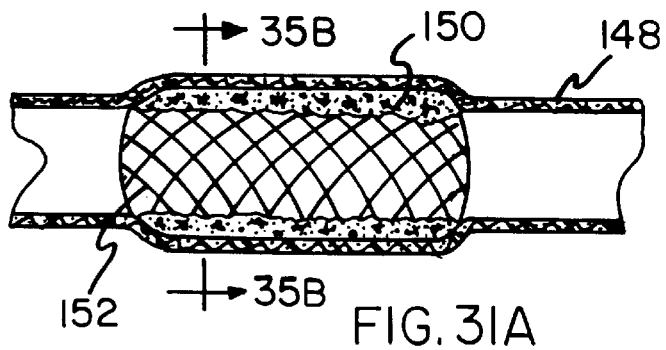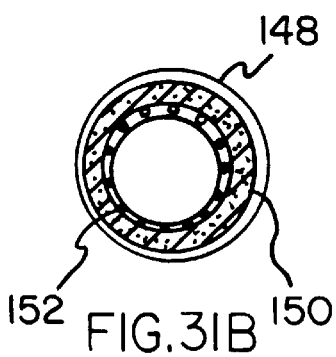
FIG. 31A  FIG. 31B $X_1 + TIME = X_n$

MULTI-STAGE EXPANDABLE STENT-GRAFT

BACKGROUND OF THE INVENTION

1. Field of the Invention

The present invention relates generally to expandable tubular devices, and particularly to implantable medical devices for use in naturally occurring or surgically created vessels, ducts, or lumens in living beings, and more specifically to catheter-delivered endoluminal stent-graft prostheses, and methods of using such devices in, for instance, cardiovascular systems.

2. Description of Related Art

Endoluminal therapies are currently under investigation as alternative methods of treating vascular disease. These approaches involve the insertion of a prosthetic device into the vasculature through a small, often percutaneous, access site in a remote vessel, followed by the intraluminal delivery and deployment of a prosthesis via transcatheter techniques. In contrast to conventional surgical therapies, endoluminal treatments are distinguished by their "minimally invasive" nature.

Endoluminal therapies have evolved to address a variety of cardiovascular pathologies. Initial outcomes of these procedures, although preliminary, are encouraging. Not surprisingly, endoluminal therapies have generated intense interest within the vascular surgery and interventional radiology communities because these techniques have the potential to simplify the delivery of therapy, improve procedural outcomes, decrease procedural costs, and broaden the patient population that may benefit from intervention.

Endoluminal stent-grafts are catheter-deliverable endoluminal prostheses comprised of an intravascular stent component and a prosthetic graft component. The function of these devices is to provide a mechanically supported intraluminal conduit that enables blood flow through pathologic vascular segments without the need for open surgery.

The stent component of the stent-graft functions as an arterial attachment mechanism and provides structural support to both the graft and the treated vascular segment. By design, stents are delivered to the vasculature in a low profile, small diameter delivery configuration, and can be elastically or plastically expanded to a secondary, large diameter configuration upon deployment. Vascular attachment is achieved by an interference fit created when a stent is deployed within the lumen of a vessel having a diameter smaller than that of the enlarged diameter of the stent.

The graft component of the stent-graft is generally constructed from a biocompatible material, such as polytetrafluoroethylene (PTFE), expanded PTFE, woven polyester, or polyurethane. The graft component has a number of proven and theoretical functions, including: segregating potential thromboemboli or atheroemboli from the bloodstream, presenting a physical barrier to mass transport between the bloodstream and arterial wall, and mitigating cellular infiltration and the host inflammatory response.

Mechanical properties play an important role in determining the performance of an endoluminal stent-graft. Since the graft component typically lacks significant structural integrity, the mechanical behavior of the stent-graft predominantly depends upon the mechanical properties of the stent component. Stents are typically classified by the type of mechanism required to induce dilatation from the delivery (small diameter) configuration, to the deployed (large diameter) configuration. Self-expanding stents are designed to spontaneously dilate (such as, elastically recover) from the delivery diameter up to a maximum, pre-determined deployed diameter. Contrastly, balloon-expandable stents are designed to be plastically enlarged over a range of sizes with the use of appropriately sized and pressurized dilatation balloons or similar devices that apply distensive force. Consequently, self-expanding stents exert a continuous, radially-outward directed force on periluminal tissues, while balloon-expandable stents assume a fixed diameter that resists recoil of the surrounding periluminal tissues.

Both types of stents have useful features. For example, in comparison to balloon-expandable stents, self-expanding stents can be rapidly deployed without the use of dilatation balloons, are elastic and therefore less prone to permanent distortion from external compression (i.e., they are resistant to permanent or plastic deformation from external compression due to their ability to elastically recover from external loads). Self-expanding stents can also radially adapt to post-deployment vascular remodeling, and retain some of the natural compliance of the vascular tissues. Since the luminal diameter of self-expanding stents cannot be adjusted (i.e., enlarged) to any appreciable degree beyond their maximum manufactured diameter, accurate sizing of the host vessel is critical. A sizing mismatch resulting in significant oversizing can cause vascular trauma, overcompression of the host vascular tissue, and/or obstructive invagination of the stent into the lumen. Undersizing, in turn, can result in a poor interference fit, inadequate anchoring, device migration, and/or leakage of blood into the peri-stent compartment. In contrast, balloon-expandable stents are more versatile when it comes to conforming to irregular vascular morphologies because their diameter can be radially adjusted through a range of diameters. However, balloon-expandable stents are prone to undesirable plastic deformation if loaded externally, which can compromise luminal diameter and blood flow.

Accordingly, it is a primary purpose of the present invention to develop an endoluminal stent-graft that maintains some of the best qualities of both self-expanding and balloon expandable stents while avoiding major deficiencies of each.

This purpose and other purposes of the present invention will become evident from a review of the following specification.

SUMMARY OF THE INVENTION

The present invention combines both self-expanding and balloon-distensible properties into a single diametrically expandable stent-graft device. One embodiment of the stent-graft of the present invention is adapted to achieve three distinct phases in use. First, the device is radially constrained on or upon a delivery device to a first diametrical dimension for insertion into a vessel. Second, when unconstrained, the stent-graft expands to achieve a second diametrical dimension within the vessel. Third, the device diameter can then be further enlarged by application of a distensive force, such as through use of a balloon dilatation catheter or via controlled creep processes engineered into the device, to variable third diametrical dimensions to fit the dimensions of the vessel or adjust to changing dimension of the vessel. During this process, the circumferential length of the graft compresses or increases with device diameter thus allowing the luminal surface to remain essentially wrinkle free. Accordingly, the stent-graft of the present invention combines the properties of both self-expanding and balloon-expandable stents into a single, easy to use device.

In a first embodiment of the present invention, a balloon-distensible graft material, such as expanded polytetrafluoroethylene (expanded PTFE), is laminated to a radially-compressed, self-expanding stent frame. By balancing (a) the inherent nature of the graft material to resist stretching beyond its original dimensions, with (b) the outward pressure exerted by the self-expanding stent frame component, the self-expanding stent will automatically assume the desired second diametrical dimension when unconstrained from the delivery device. To achieve distention beyond this second diametrical dimension, the graft material is selected to deform to variable third diametrical dimensions with application of sufficient distensive force. Sufficient distensive force may be applied over relatively short periods of time (e.g., force applied by a balloon dilatation catheter) or lower forces applied over relatively long periods of time (e.g., force applied by the self-expanding stent in-situ resulting in radial creep distention of the graft component). Since the preferred stent component is self-expanding, its diameter will essentially match that of the graft material.

A second embodiment utilizes the same principles as described previously, except that the self-expanding device is maintained at its introductory profile using an integral constraining lamina. This embodiment is balloon-mounted and balloon-deployed yet retains the elastic properties of the self-expanding structural component. The self-expanding stent is attached to a balloon distensible graft component having a diameter essentially equal to the first functional diameter and is prevented from expanding by the graft component or integral constraining lamina (i.e., outward radial force exerted by the stent is less than the circumferential radial strength of the graft component or lamina). This device can then be mounted upon a balloon dilatation catheter. The device is delivered to the deployment site in a manner consistent with current delivery techniques and is deployed via inflation of the balloon. During inflation, the graft component or integral constraining lamina yields or is disrupted by the balloon (i.e., increasing pressure). Following yielding or disruption of graft component or the integral constraining lamina, the diameter of the device enlarges via continued balloon dilatation augmented by the continuous, radially directed forces exerted by the self-expanding stent. Since the graft component undergoes circumferential elongation proportional to the diameter of the device, a wrinkle free or otherwise essentially smooth luminal surface is maintained throughout all functional diameters.

After the appropriate diameter is achieved, the balloon can be deflated and the luminal surface remains smooth. The self-expanding stent exerts a continued outward radial force that is exerted on 1) the graft component and/or integral constraining lamina, (thereby preserving a smooth luminal surface) and 2) the vessel wall. With time, the lumen may narrow due to normal or pathological healing. To counteract this narrowing, the stent-graft can increase in circumferential length via creep processes resulting from the outward radial force supplied by the self-expanding stent while retaining a smooth luminal surface. Also, the stent-graft can be progressively balloon dilated to larger functional diameters up to the maximum manufactured diameter of the self-expanding stent.

The device of the present invention provides a number of distinct advantages over previous expandable stent-graft devices. For example, the mechanism of dilatation can be varied in one or more distinct regions along the length of device allowing a uniquely customized fit within the vessel. Further, the radial strength of the device can be varied in one or more distinct regions along the length of the device. Further, the device of the present invention provides the clinician with a range of essentially wrinkle-free functional diameters, and can be engineered to enlarge over time to compensate for the effects of luminal narrowing due to normal or pathological healing (herein referred to as "compensatory enlargement"). Additionally, the device of the present invention provides its adjustable distension properties without undergoing significant shortening in length thus providing better control of device placement and deployment. These and other benefits of the present invention will be appreciated from review of the following descriptions.

DESCRIPTION OF THE DRAWINGS

The operation of the present invention should become apparent from the following description when considered in conjunction with the accompanying drawings, in which:

FIG. 28A is a longitudinal cross-section view of a blood vessel having a focal stenosis;

FIG. 28B is a transverse cross-section view of the blood vessel of FIG. 28A along line 28B—28B;

FIG. 29A is a longitudinal cross-section view of the blood vessel shown in FIGS. 28A and 28B, with a stent-graft device of the present invention mounted over an angioplasty balloon catheter therein positioned in preparation of deployment;

FIG. 29B is a transverse cross-section view along line 29B—29B of FIG. 29A;

FIG. 30A is a longitudinal cross-section view of the blood vessel shown in FIGS. 28A and 28B, with the stent-graft device of the present invention in the process of being deployed over the stenosis;

FIG. 30B is a transverse cross-section view along line 30B—30B of FIG. 30A;

FIG. 31A is a longitudinal cross-section view of the blood vessel of FIGS. 28A and 28B with the stent-graft device of the present invention shown fully deployed;

FIG. 31B is a transverse cross-section view along line 31B—31B of FIG. 31A;

DETAILED DESCRIPTION OF THE INVENTION

The present invention comprises an improved expandable tubular device that can be used to establish and maintain a fluid conduit. The preferred device of the present invention comprises a stent-graft for use in human or other animal implantation to form and/or maintain a fluid conduit, such as in an endovascular application. Additionally, as is explained in greater detail below, the device of the present invention can also be used to control the amount or velocity of fluid flow through a conduit, to block unwanted flow into or out of the conduit, and/or to redirect flow within the conduit.

Figure 1:
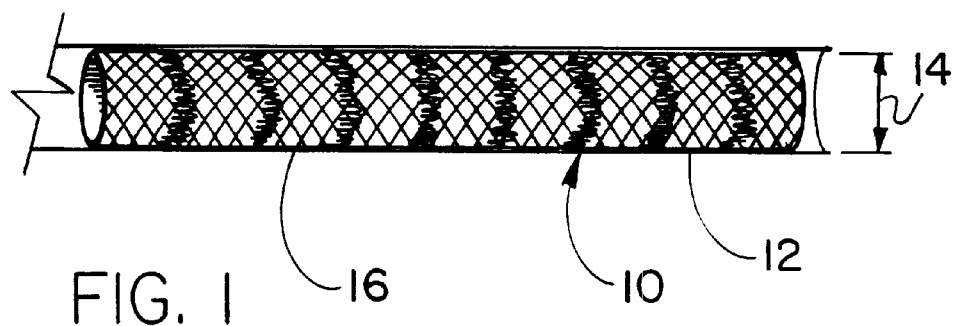
FIG. 1 is a side elevation view of one embodiment of a stent-graft device of the present invention, shown in its compacted first dimension inside its restraining element (shown in transverse cross-section)
Figure 2:
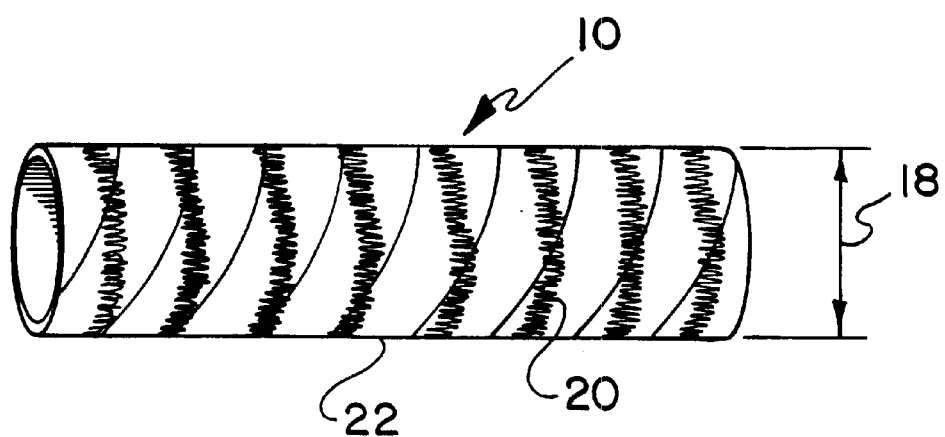
FIG. 2 is a side elevation view of the embodiment of the stent-graft of FIG. 1 shown in its enlarged, self-expanded second dimension.
Figure 3:
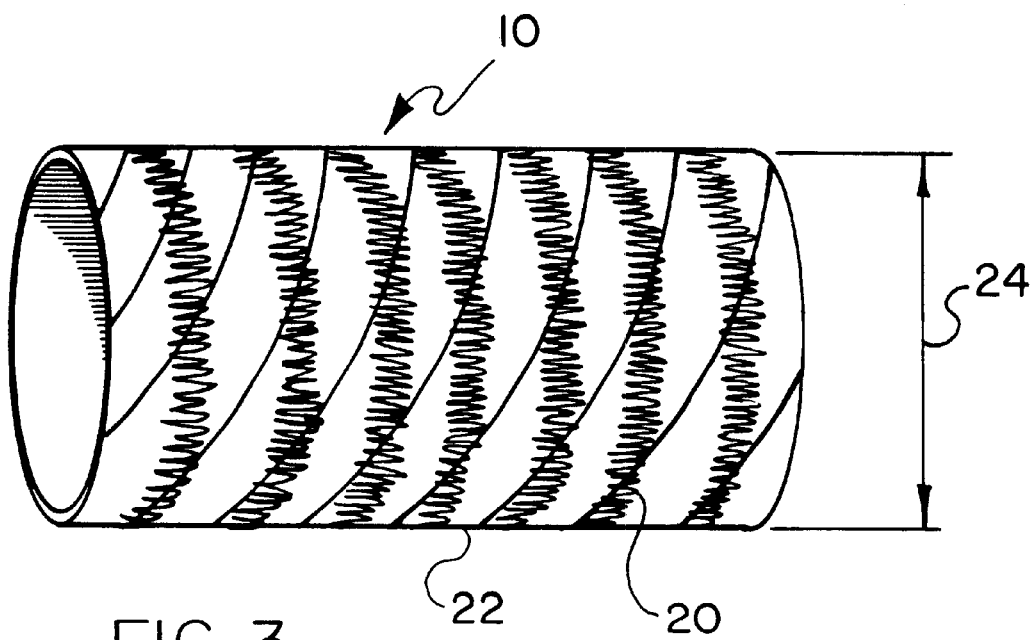
FIG. 3 is a side elevation view of the embodiment of the stent-graft of FIG. 1 shown in an enlarged, balloon-expanded third dimension.

As is illustrated in FIGS. 1 through 3, the device 10 of the present invention comprises an essentially tubular component 12 that is adapted to assume, when desired, at least three distinct dimensions in use. As is shown in FIG. 1, the device 10 may be first compacted into a small transverse cross-sectional first diametrical dimension 14. As is explained below, since the device is self-expanding, to maintain the first dimension the device 10 must be constrained, such as through insertion within a catheter tube 16 or similar device or through other constraining means (such as one or more external constraining threads, a "corset" constraining membrane or sheet, sacrificial constraining rings, threads, sheets, or other constraint, or similar devices). The first readily inserted into a dimension 14 should be sufficiently compact that the tube 16 and device 10 can be delivered to an intraluminal location for deployment.

As is shown in FIG. 2, once the device 10 is no longer radially constrained by the constraining means the device 10 will automatically expand to an enlarged second diametrical dimension 18. Self-expansion is accomplished by providing a stent element (or "support structure") 20 within the device that has at least some degree of shape "memory," causing it to elastically recover or otherwise enlarge once it is no longer constrained. This expansion may also occur through other means, such as through: internal inflation devices; expandable frames; thermal, electrical, magnetic or chemical induced enlargement; etc.

However, the device 10 also includes a polymer sleeve 22 attached to the stent frame element 20 that restricts the expansion of the device 10 to a pre-determined size comprising the second dimension 18. Although the stent frame 20 may be capable of further self-expansion beyond the second dimension 18 if not restrained, it is the intent of the present invention to substantially limit its self-expansive properties, by combining it with the graft component 22.

In the second dimension 18, the device 10 is self-supporting and resistant to external compression. By the term "self-supporting," it is meant that the device 10 will retain the shape and size of the second dimension 18 without the need for a separate structure (such as struts or clamps), anchorage devices (such as sutures, adhesives, or other means), or an increased relative internal pressure differential to maintain the device at the second dimension 18. By the term "resistant to permanent deformation from external compression," it is meant that once the device 10 expands to its second dimension it will not easily collapse when an external force is applied to it and will elastically recover from most external deformations (contrasted with, for example, an unsupported expanded polytetrafluoroethylene vascular graft tube that will easily and fully collapse when squeezed between a person's fingers) and it will readily return to the second dimension once the external force is removed.

Once the device 10 assumes its second dimension 18, it is often desirable to enlarge all or portions of the device 10 to a still larger third diametrical dimension 24, as is shown in FIG. 3. In order to accomplish enlargement beyond the second dimension 18, the device 10 is adapted to respond to a distensive force that causes the polymer sleeve 22 to stretch beyond the second dimension to the third dimension 24. It should be noted that the stent frame will self-expand without plastic deformation up to a maximal, pre-determined diameter significantly larger than the second diameter 18. Ideally, the device 10 is adapted to expand when subjected to the distensive force of an endovascular balloon, an endovascular mechanical dilator, or similar device. Diametrical expansion, furthermore, is not accompanied by excessive shortening in the length of the device. The device should maintain its third dimension 24 with minimal recoil once the distensive force is removed.

One important benefit of the device of the present invention is that it undergoes minimal longitudinal shortening in length when expanding between its first diametrical dimension to its second diametrical dimension and when expanding between its second dimension and its third dimension. As the term "minimal longitudinal shortening" is used herein, it defines a condition wherein the device does not shorten more than 15% of its length when distending between an insertion diameter and an operative diameter, and preferably it does not shorten more than 10% of its length, and even more preferably it does not shorten more than 7%, and even more preferably no more than 3 to 5%, and most preferably less than 3%.

Another important benefit of the present invention is that it provides an essentially wrinkle-free luminal surface between at least the second and third dimensions. As is explained in greater detail below, by providing a graft material that yields or stretches (or otherwise expands smoothly in the circumferential direction) when distended, the resulting luminal surface will remain essentially free of wrinkles or corrugations. In fact, the preferred expanded PTFE graft material taught herein can provide essentially wrinkle-free structure between the first and third dimensions. It is believed that such wrinkle-free luminal surface provide improved flow dynamics in vivo.

Additionally, if not dilated to the maximum (i.e., unrestrained or "manufactured") diameter of the self-expanding stent, the diameter of the device can be designed to increase over time ("creep") up to the maximum diameter of the stent. This intentional creep-expansion may be beneficial to accommodate enlargement of the blood vessel or luminal narrowing over time. This is believed to be very beneficial for implants in children to accommodate natural growth patterns. Additionally, it is believed that such creep-expansion may be beneficial to accommodate growth of diseased vessels while preventing uncontrolled distention and possible rupture.

The device 10 of the present invention preferably undergoes a substantial change in dimensions between the first diametrical dimension and the second diametrical dimension, and again between the second diametrical dimension and the third diametrical dimension. For instance, for many vascular applications it is desirable that the device at least approximately doubles in diameter between the first and second dimensions, and is capable of being approximately doubled again in diameter between the second dimension and the fully dilated third dimension.

It should be appreciated that the exact dimensions of the first, second, and third diametrical dimensions may be readily modified to accommodate various clinical, anatomical, and/or physiological demands. For example, the expansion from the first to second diametrical dimension may comprise a growth of about 10, 20, 30, 40, 50, 60, 70, 75, 80, 90, 100 or more percent. Similarly, the expansion from the second to the third diametrical dimension may likewise comprise a growth of about 1, 2, 5, 7, 10, 20, 30, 40, 50, 60, 70, 75, 80, 90, 100 or more percent. For many applications the initial growth from the first to the second dimensions will generally be fairly large, for example about 100 to 400 percent or more. While the growth from the second to the third dimension may comprise only about less than 10, 20, 30, 35, 40, 45, or 50 percent or more.

As is explained in greater detail below, in some applications it is desirable that the device 10 be configured to resist expansion beyond the second dimension 18 at the time of implantation (or installation) until a threshold distensive force is reached. At that point, it is desirable that the device 10 can be expanded to a variety of different third dimension proportions to allow for customized sizing of the device, including achieving precise deployed diameters and/or deploying the device with varying diameters along its length.

Thus, it should be appreciated that the device of the present invention combines many of the desirable features of both self-expanding stent devices and balloon expandable devices. Like a self-expanding stent, the device of the present invention assumes an enlarged diameter immediately upon deployment, making its initial placement easy to accomplish. Additionally, also like a self-expanding stent, the device 10 of the present invention is resistant to external pressures, making it crush resistant and supplying additional support for the device when deployed in place. However, like a balloon-expandable stent, the device 10 of the present invention can be very accurately deployed with customized sizing of the device diameter in-situ. As is explained in greater detail below, the hybrid device of the present invention allows for a wide variety of unique applications that would be difficult or impossible to achieve with a endoprosthesis that has only self-expanding or balloon distensible properties.

It should be evident from the above description that the device of the present invention may be employed in a conventional manner of self-expanding stent-graft, fully deployed at its second dimension where appropriate.

For many applications, it is preferred that the device of the present invention achieves its enlarged dimensions with controlled creep dilatation. It is also desirable that the device undergo minimal longitudinal shortening during expansion. In particular, preferably the device made in accordance with the present invention may experience a radial creep (that is, slow growth in the radial dimensions of the device over time in response to pressures (either (or both) physiological and those exerted by the self-expanding stent) applied to the device. This feature provides "compensatory enlargement" of the luminal geometry over time, allowing the diameter of the blood flow conduit to be preserved, despite the encroachment of hyperplastic tissues resulting from the healing and incorporation processes.

Figure 4:
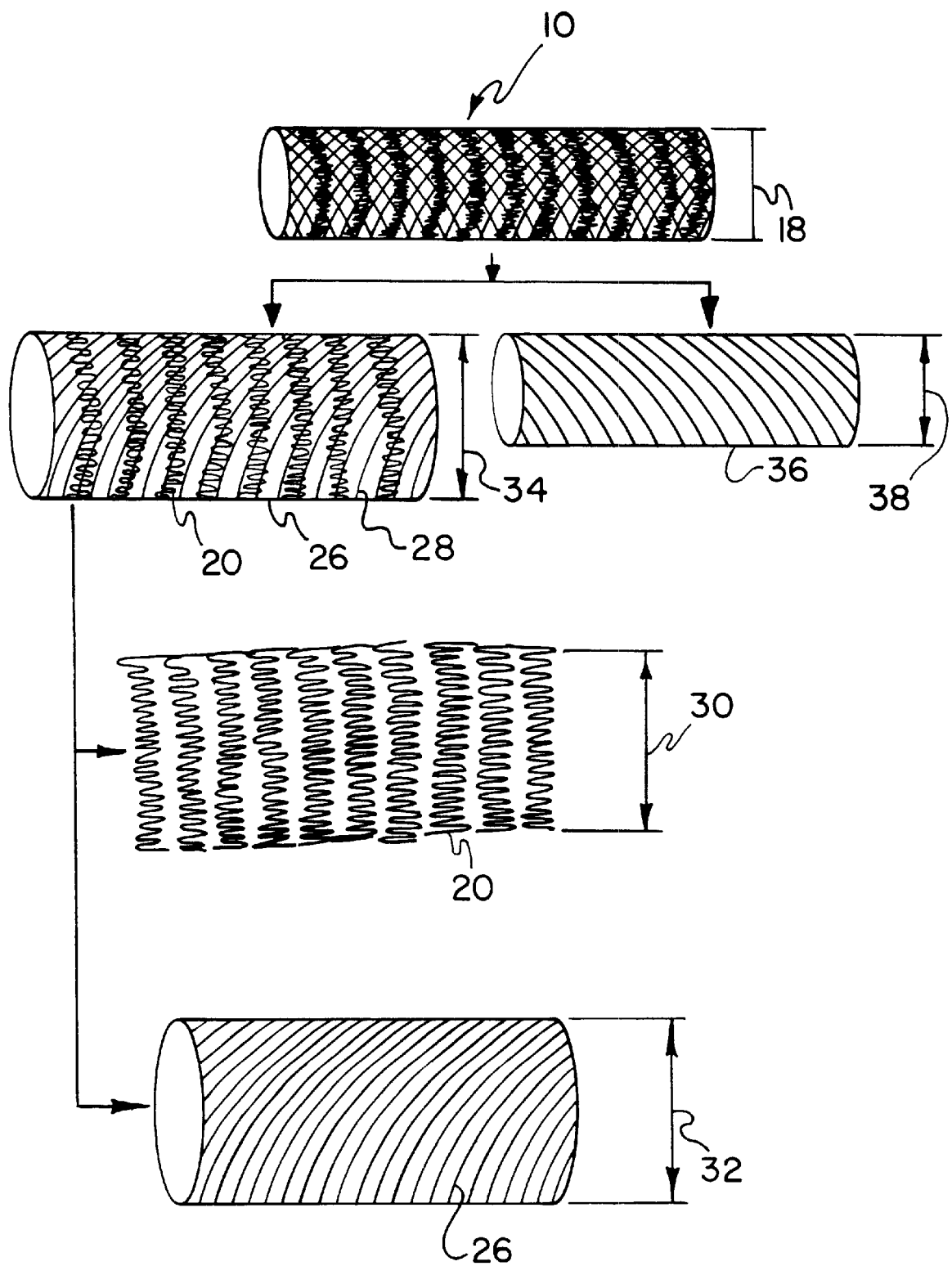
FIG. 4 is an exploded side elevation view of a stent-graft device of the present invention, illustrating individual stent frame and graft components of the device.

Creating a device having hybrid expansion properties (i.e., being both self-expanding and balloon-expandable) in the present invention is accomplished by combining components having balanced expansion and restrictive properties. As is shown in FIG. 4, the preferred device 10 of the present invention may comprise a number of component parts. The device 10 begins by attaching together a self expanding stent frame element 20 to an auxiliary sleeve (or "graft") element 26 to form a first component part 28.

The stent frame element 20 should be constructed in a manner and from a material that allows the frame 20 to be compressed to significantly smaller sizes while having sufficient "memory" to return to a pre-determined orientation, such as a plastic, metal (e.g., nitinol or stainless steel), or similar material. The preferred stent frame 20 comprises a nitinol metal device such as that disclosed in WO97/21403 to Martin, et al., incorporated by reference. The stent frame 20 may be constructed either to expand indiscriminately or it may be designed to have a well-defined maximum expanded dimension 30.

The stent frame 20 is preferably attached, such as through adhesive, tape, or heat set with thermoplastic or thermosetting material, to the graft element 26. The polymer sleeve 20 or graft element 26 may be attached to either the outside or the inside of the stent frame 20 (or both inside and outside the stent element 20). Preferably, the graft element should be attached to the inside (that is, the luminal surface) of the stent frame 20.

The polymer sleeve 22 or graft element 26 preferably comprises a biocompatible polymer that attaches to the stent frame 20 and isolates the frame 20. As such, the graft element 26 may comprise polytetrafluoroethylene (PTFE), porous PTFE or other porous polymer, expanded PTFE (porous or non-porous), or other polymer material, such as polyethylene, polyurethane, nylon, PFA, amorphous PTFE, ETFE, polypropylene and polyamides. For most applications the graft material should be bio-compatible. The polymer material may be constructed as a seamless tube or it may be wrapped (e.g., either helically or longitudinally) to form a tube. Alternatively, it may comprise a composite of one or more seamless tubes, layers of film, or combination of tubes and films. The graft element may be formed into a tube before attachment to the stent frame 20 or it may be wrapped around the stent frame 20 to form the tube.

In addition to isolating the stent frame 20, the graft element 26 also can serve to limit the ultimate extent of expansion of the device 10. As is shown in FIG. 4, the graft element 26 is formed from a material that has a maximum dimension 32. In other words, the graft element 26 is formed from a material that will resist any radial expansion beyond maximum dimension 32. Once attached to the stent frame 20, the maximum dimension 32 of the tube will limit the stent frame 20 from radial expanding beyond maximum dimension 32. The maximum dimension 32 of the graft element 26 can be used with a stent frame 20 with indiscriminate expansive properties to control the ultimate expansion of the device 10, or it can be used in conjunction with a stent frame 20 having a maximum dimension 30 to provide a double restriction on ultimate expansion of the device.

Formed in this manner, the first component part 28 comprises a covered, lined, or covered and lined stent frame that can be compressed into smaller dimensions, but which will demonstrate a consistent tendency to expand to a maximum dimension 34. This maximum dimension 34 should approximately correspond to a third diametrical dimension 24 previously described with regard to FIG. 3, and is similar in magnitude to diameters 30 and 32.

In order to then cause the device to establish the second dimension 18 previously described with respect to FIG. 2, a distensible sleeve element 36 is employed. This distensible sleeve element 36 may be constructed in the same manner as previously described with respect to the graft element 26. The difference is that the distensible sleeve element 36 is formed to have a first operative dimension 38 approximately corresponding to the second dimension 18. Additionally, the distensible sleeve element 36 has the ability to be deformed beyond its first operative dimension through the application of more than a threshold distensive force therein.

Preferably, the distensible sleeve element 36 is constructed from a material that will deform beyond the first operative dimension 38 through a range of second operative dimensions up to at least maximum dimension 34. Through this deformation process, the distensible sleeve element 36 should ideally retain each of the second operative dimensions until further distensive force is applied thereto. In other words, if at the time of implantation, the first operative dimension 38 of the distensible sleeve element 36 is a diameter of 4 mm, once distensive force over a threshold amount is applied thereto causing it to expand to 5 mm, it will stay at 5 mm until further distensive force over a threshold amount is applied to cause it to expand further (e.g., to 5.5 mm, or 6 mm, or 6.5 mm, etc.). This property is referred to herein as being "selectively expansive."

The preferred distensible sleeve element 36 comprises a distensible tube, such as the expanded PTFE tube described in U.S. Pat. Nos. 3,953,556, 3,962,153, 4,096,227, 4,187,390, and 4,902,423, to Gore, all incorporated by reference.

By contracting the first component part 28 to approximately the first operative dimension 38 and bonding the primary distensible sleeve element 36 to the first component part 28, the device 10 of the present invention is formed. The primary distensible sleeve 36 can be bonded to the inside of the stent 20 and/or to the outside of the stent 20. Alternatively, the sleeve 36 may be integral with the graft component 26. The result is that the device can be mechanically compacted to the first dimension 14, as is shown in FIG. 1, and it will automatically expand to the second dimension 18 once the compacting force is removed. However, the distensible sleeve element 36 will resist any further expansion of the device 10 beyond this second dimension 18 until a distensive force over the threshold amount is applied.

By applying a distensive force over the threshold amount using a balloon or other dilation device, the device 10 can be selectively increased beyond the second dimension through a range of third dimensions 24. The selectively expansive properties of the distensible sleeve element (i.e., the ability of the distensible sleeve element to resist further dilation at each of its second operative dimensions) assure that the device 10 will not expand beyond each set third dimension until further dilation force is applied. In this manner, the device of the present invention can combine both self-expanding properties and balloon-expanding properties into a single unit.

It should be appreciated that while use of the graft element 26 is preferred for many applications, the present invention may function adequately by simply employing a stent frame 20 alone in conjunction with the distensible sleeve element 36. In this manner, the device will still exhibit both self-expansive properties to the second dimension 18 and selectively expansive properties beyond the second dimension 18 through the range of third dimensions 24.

One method for constructing a device 10 of the present invention is described below.

An outer circumferential surface of the distensible sleeve element 36 is coated with a uniform lamina of thermally activated adhesive. The distensible sleeve element 36 is mounted on a radially expandable mandrel overlying a disposable "cushion tube." The interpositional cushion tube provides a barrier between the mandrel and the distensible sleeve element 36. This creates a first assembly.

Stent-graft comprising a stent frame 20 and a graft element 26 (similar to sleeve element 28 in FIG. 4) is radially constrained within a capture tube. The frame 20 and sleeve 26 are selected to self-expand to a maximal, predetermined luminal diameter, and not to undergo appreciable longitudinal shortening during this self-expansion. The capture tube should have an inner diameter less than the maximal diameter to which the stent-graft will expand and approximately equivalent to an outer diameter of the balloon-distensible graft/radially-expandable mandrel assembly. This creates a second assembly.

The first assembly is inserted into the second assembly. The first assembly is then radially expanded to create an interference fit between the inner graft material of the radially constrained conventional stent-graft 44 and the outer circumferential surface of the distensible sleeve element 36. This creates a third assembly. Alternately, the interference fit may be achieved by swaging an appropriate size mandrel/cushion tube directly into the first assembly, or by slowly removing the stent-graft from the capture tube and wrapping it tightly with a constraining material.

This entire third assembly is heat treated at a temperature sufficient to activate the adhesive on the distensible sleeve element 36, and cause permanent bonding of the distensible sleeve element to the inner surface of the radially constrained stent frame 20 and sleeve 28 components to form the stent-graft 10 of the present invention. Once the stent-graft 10 is created, the mandrel can be contracted and removed from the capture tube to free the stent-graft 10 from the third assembly. The stent-graft 10 formed in this manner can then be used as previously described.

It should be appreciated that these construction techniques can be readily modified to create different embodiments of the present invention. For example, sleeve components can be provided on both sides of the stent frame 20 to provide for complete coverage of the stent component. As has been noted, however, the present invention may function quite adequately by only using a single sleeve component inside or outside of the stent frame. Additionally, it may be desirable to provide one or more radio-opaque markers on or within the device 10 to facilitate accurate delivery and deployment.

Figure 5:
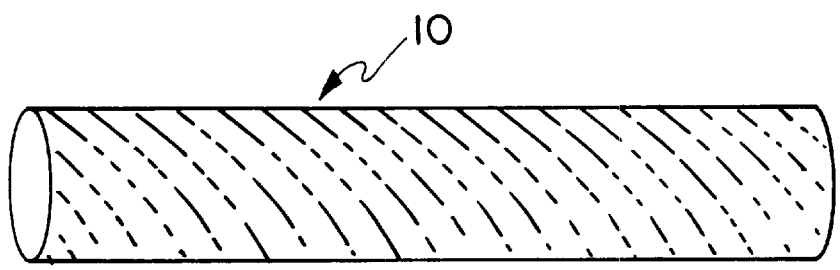
FIGS. 5 through 9 illustrate examples of stent-graft devices of the present invention in various configurations of self-expanding and balloon expanding regions along the same device.
Figure 6:
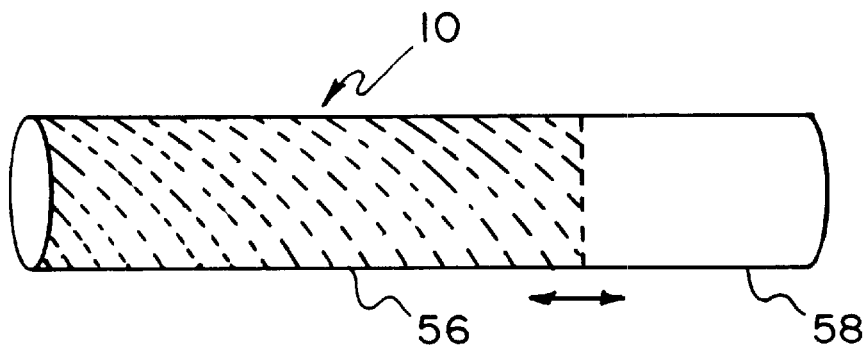
Figure 7:
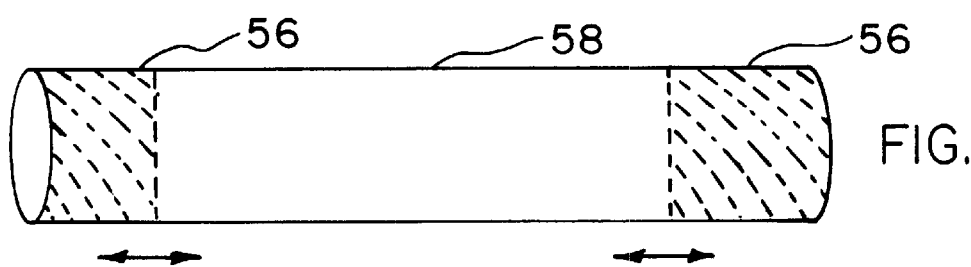
Figure 8:
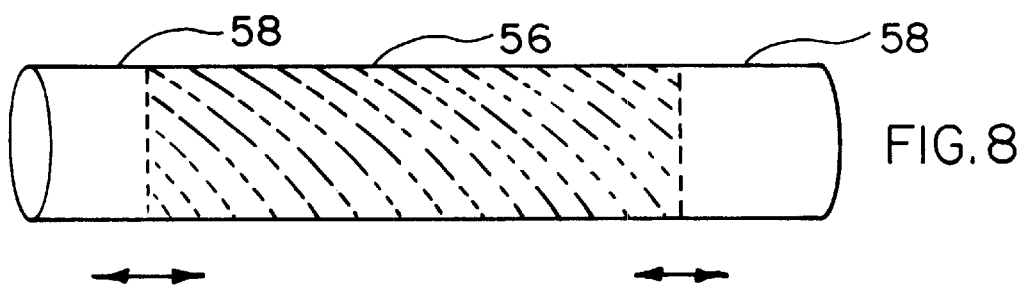
Figure 9:
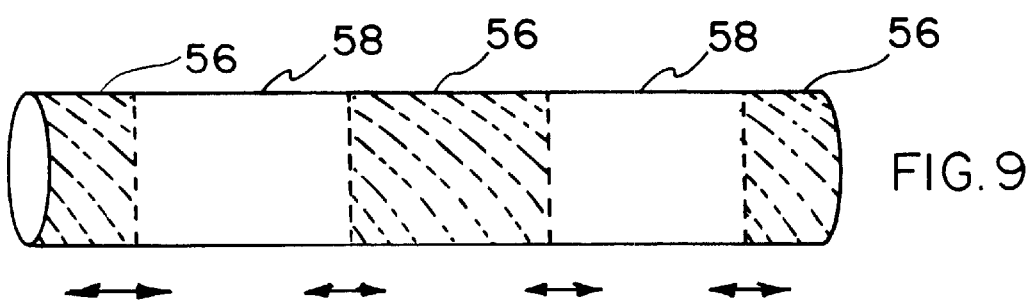

Still other examples of modifications for the device 10 of the present invention are described below. FIGS. 5 through 9 illustrate various embodiments of a device 10 of the present invention that employ different constructions along the length of the device 10. FIG. 5 illustrates a device 10 that has a consistent construction along its entire length that is both self-expanding and balloon dilatable. By contrast, FIGS. 6 through 9 illustrate various constructions of devices 10 that include a self-expanding and balloon distensible section 56 and a section 58 that is self-expanding only. Constructed in this manner, the device 10 can be "programmed" to have particular flow characteristics and/or to be safely deployed in certain applications where it is not desirable to have the entire device fully dilated. It should be further appreciated that these modified devices may likewise include segments that are self-expanding and segments that are not self-expanding, again programmed for particular applications where consistent-graft performance along the length of the graft is not preferred.

Figure 10:
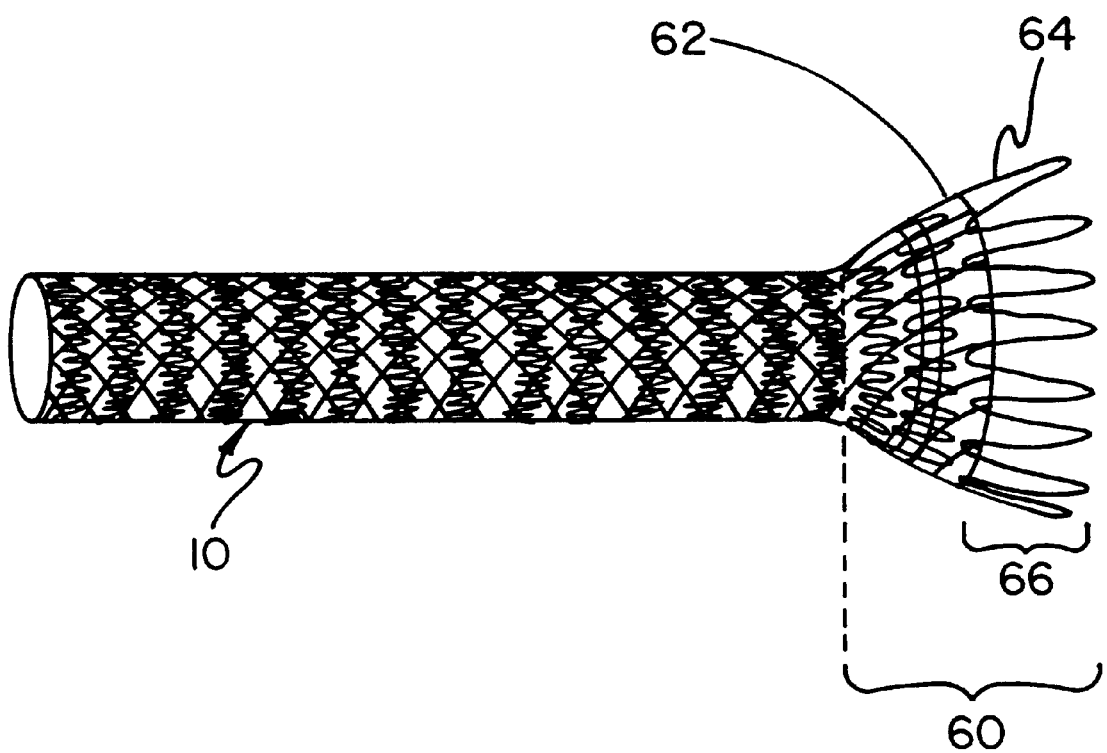
FIG. 10 is a side elevation view of another embodiment of an expandable stent-graft device of the present invention, the device including a flange segment and a marker locator means therein.

Still another embodiment of the device 10 of the present invention is illustrated in FIG. 10. In this instance, one or more anchoring mechanisms 60 are provided to facilitate accurate deployment, and resist migration or longitudinal displacement of the deployed device. In the embodiment illustrated, the anchoring mechanism 60 comprises a "flared" end that can be placed into an enlarged end of a vessel or through an opening into or out of a vessel to hold the device 10 in place. It should be evident that anchorage may likewise be improved with the use of barbs, hooks, bioadhesives, or other measures. This embodiment may also include one or more markers 62, 64 to allow for exact positioning and deploying of the device under fluoroscopic conditions. This embodiment also illustrates a hybrid covering of the device, whereby most of the device is fully covered whereas one end includes an uncovered segment 66.

As has been described, it is desirable that the stent-graft device 10 of the present invention be constructed from a material that will not begin dilating at the time of implantation until a threshold force is reached. It is further desirable that after the threshold force is met, the device will only dilate to the extent caused by the threshold force and will not dilate further unless and until a further dilating force is applied. These properties are illustrated in the graphs of FIGS. 11 and 12.

Figure 11:
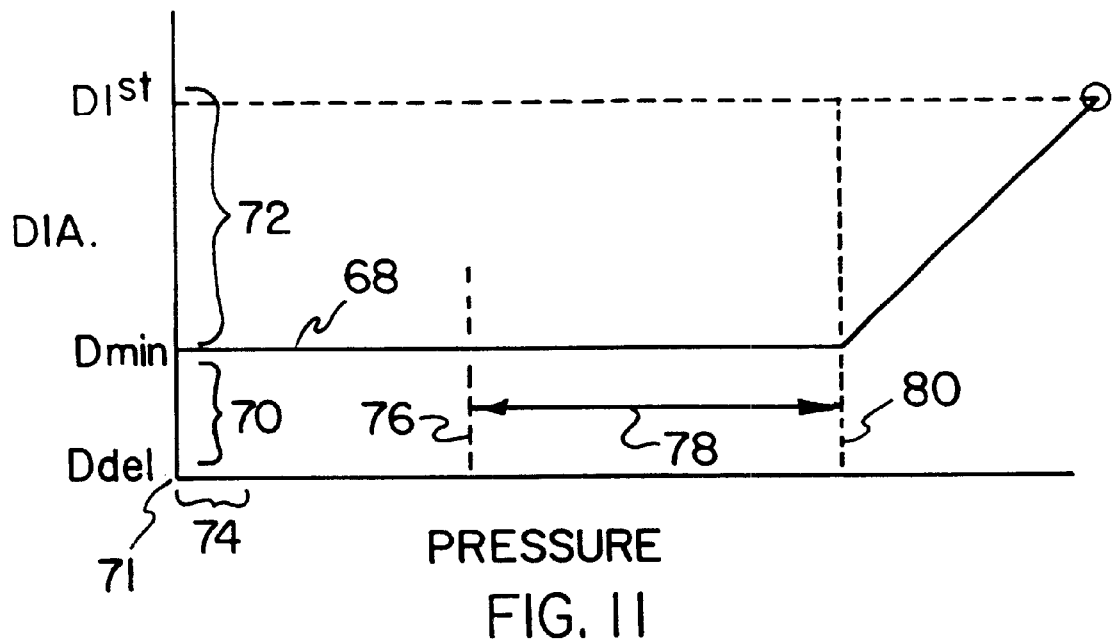
FIG. 11 is a graph plotting diameter verses pressure for one embodiment of a stent-graft device of the present invention.

FIG. 11 plots the diameter versus pressure of a stent-graft of the present invention. The performance of the device of the present invention is represented by line 68. The graph illustrates an initial delivery diameter 71, a self-expanded diameter 70, and a balloon expanded diameter 72. At normal physiological ranges of pressure 74, the device will assume a self-expanded diameter 70, when no radial constrictive forces are applied such as by delivery catheter. The radial pressure exerted by the stent frame component of the graft is represented at line 76. Preferably the device includes a factor of safety 78 wherein additional pressure can be applied to the device without any substantial dilation of the device. However, once a threshold pressure is achieved, represented by line 80, then the device will steadily increase in diameter as additional pressure is applied to the graft. This diameter increase can be designed to increase steadily up to a maximum diameter, or it can be designed to reach one or more plateaus during the balloon expansion process.

Figure 12:
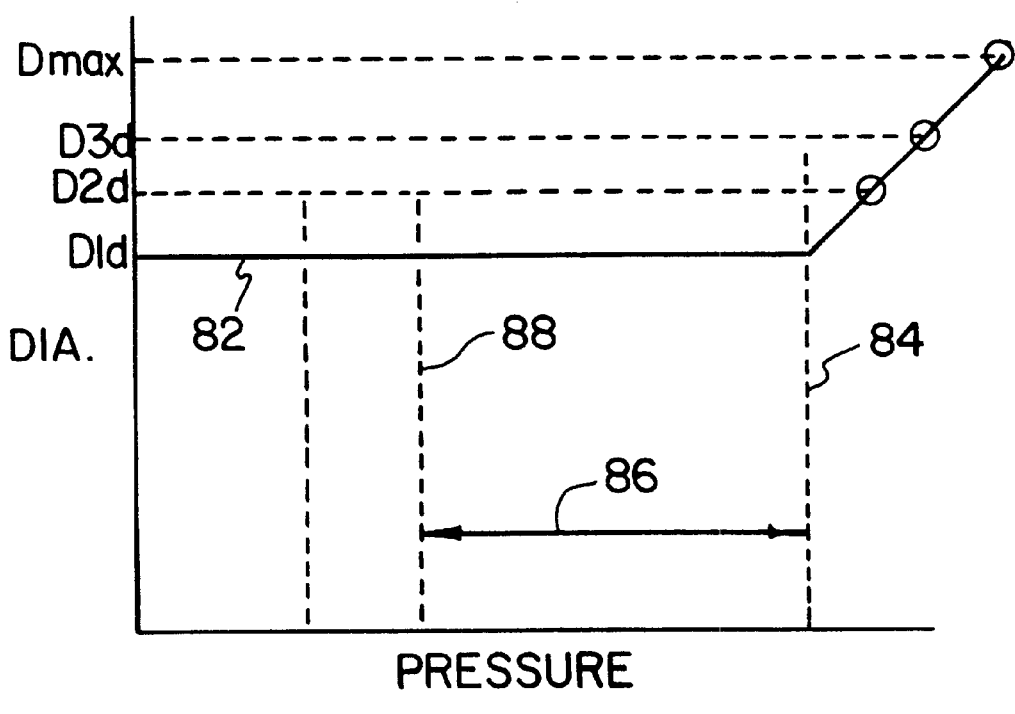
FIG. 12 is a graph plotting diameter verses pressure for another embodiment of a stent-graft device of the present invention.

FIG. 12 plots the diameter versus pressure of a stent-graft device of the present invention from a first diameter reached in accordance to FIG. 11 up to a maximum diameter. As is shown, this device is designed to maintain the first diameter along line 82 until a threshold pressure is reached, represented by line 84. This plateau includes a factor of safety 86 between a normal radial pressure exerted by the stent component of the device, illustrated by line 88, and the threshold pressure 84. Once the threshold pressure 84 is reached, again the diameter increase can be designed to increase steadily up to a maximum diameter, or it can be designed to reach one or more additional plateaus during the balloon expansion process.

Figure 13:
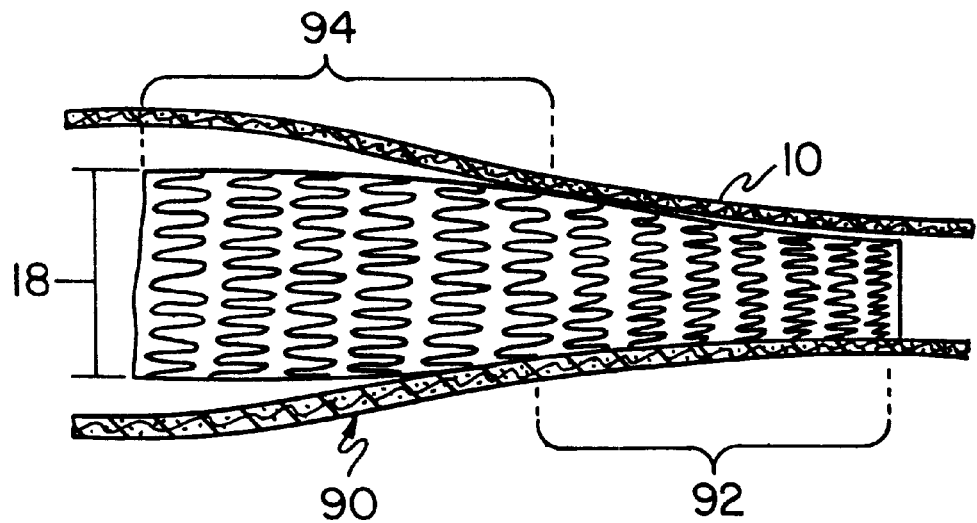
FIG. 13 is a cross-section view of a tapered vessel illustrating insertion of a stent-graft device of the present invention, the device having assumed a first functional diameter therein.
Figure 14:
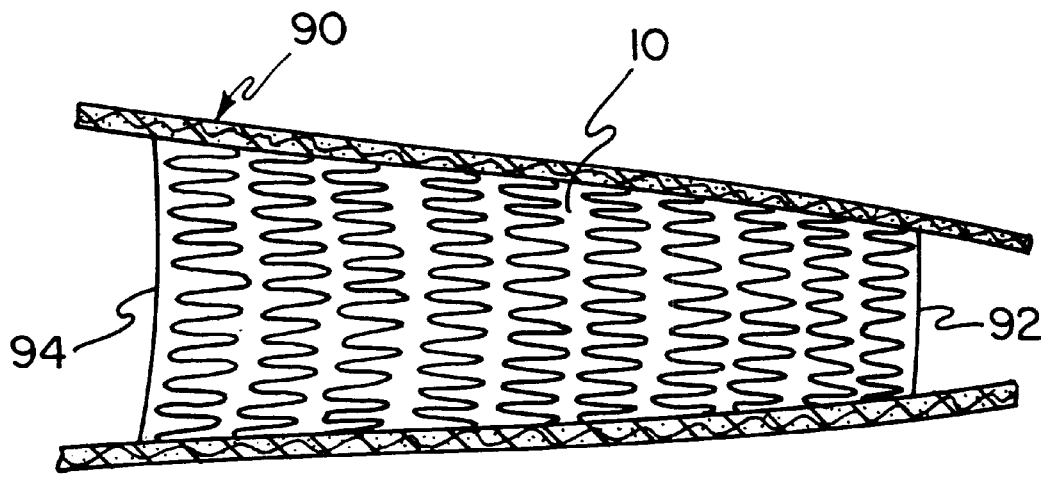
FIG. 14 is a cross-section view of the constricted vessel of FIG. 16, with the device having been selectively expanded to a second functional diameter to match the dimensions of the vessel.

The device 10 of the present invention can be adapted to address many different situations requiring a self-expanding and further dilatable stent device. Examples of such uses are illustrated in FIGS. 13 through 22. FIGS. 13 and 14 show how the device of the present invention can be employed inside a tapered conduit 90. As is shown in FIG. 13, the device 10 assumes a self-expanded position within the tapered conduit 90, with a proper fit on a first end 92 of the device and a loose fit on a second end 94 of the device (that is, the device will only expand up to its second dimension 18 on the second end of the device).

As is shown in FIG. 14, the device 10 can then be balloon expanded to provide a proper fit along the entire length of the device, with the second end 94 expanding to snugly meet the interior diameter of the conduit.

Figure 15:
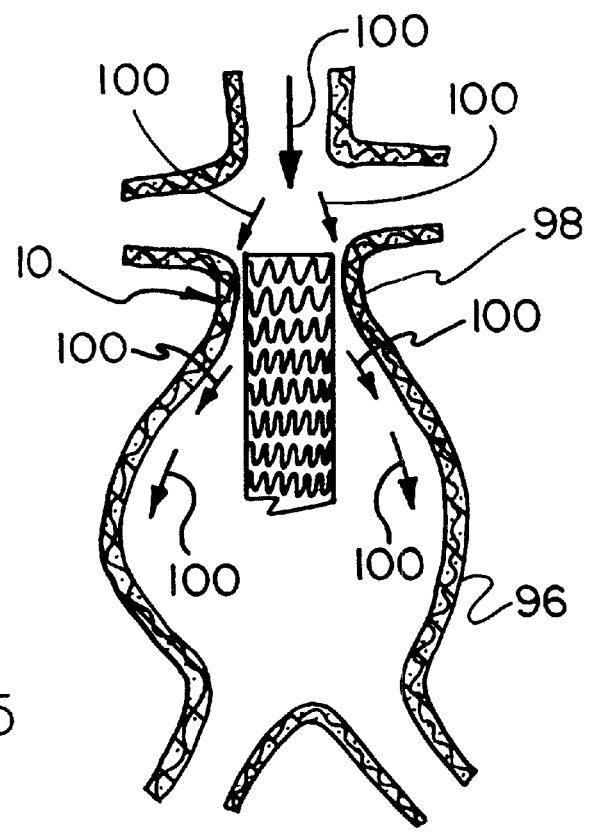
FIG. 15 is a cross-section view of an aneurysmal defect in a vessel, with a stent-graft device of the present invention, shown segmented, having been positioned therein and having assumed a first functional diameter.
Figure 16:
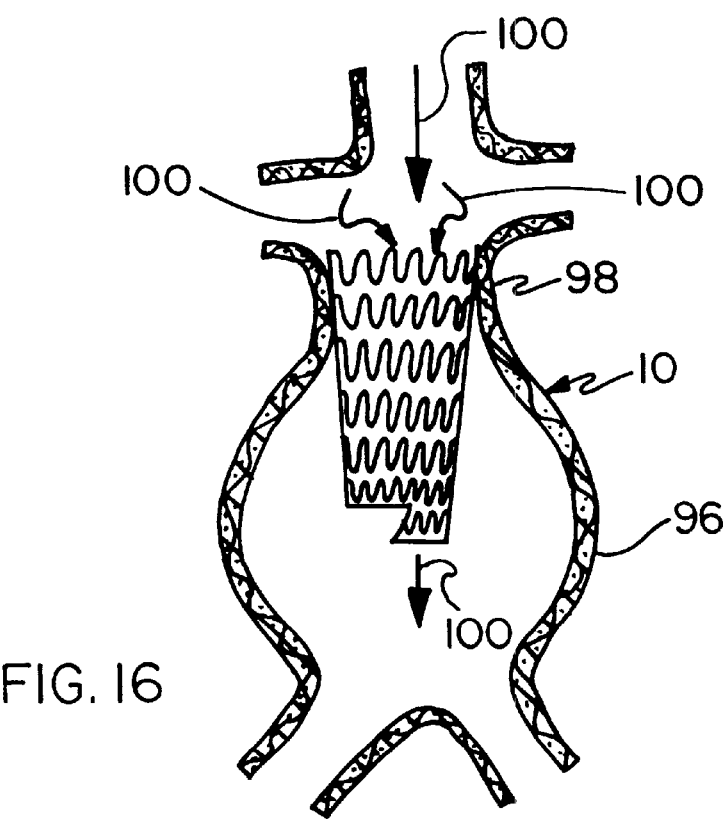
FIG. 16 is a cross-section view of the vessel of FIG. 18, wherein the device has been expanded to a second functional diameter to prevent leakage around the outside of the device.

FIGS. 15 and 16 show how the device can be used to prevent endo-leakage. FIG. 15 illustrates a device of the present invention (which may comprise a component part of a further device, such a bifurcated stent-graft adapted to direct flow through the illiac arteries) mounted within an aneurysmal compartment 96 in a blood vessel 98. The device 10 is in its self-expanded orientation within the compartment 96 (analogous to dimension 18). Since there is not a tight fit between the device 10 and the blood vessel 98, blood flow, indicated by arrows 100, is leaking around the device 10. This condition is referred to as "endo-leakage." As is shown in FIG. 16, by dilating the device 10 to a larger diameter analogous to dimension 24, a tight fit can be established between the device 10 and the blood vessel 98. This directs all of the blood flow 100 through the device 10, as is desired.

Figure 17:
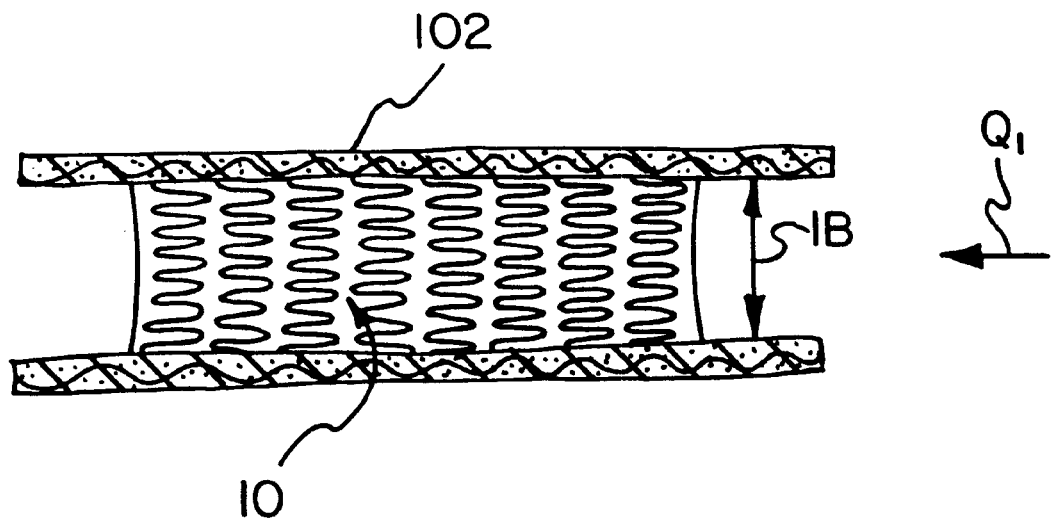
FIG. 17 is a cross-section view of a vessel showing the initial deployment of a stent-graft device of the present invention therein, the stent device having assumed a first functional diameter therein.
Figure 18:
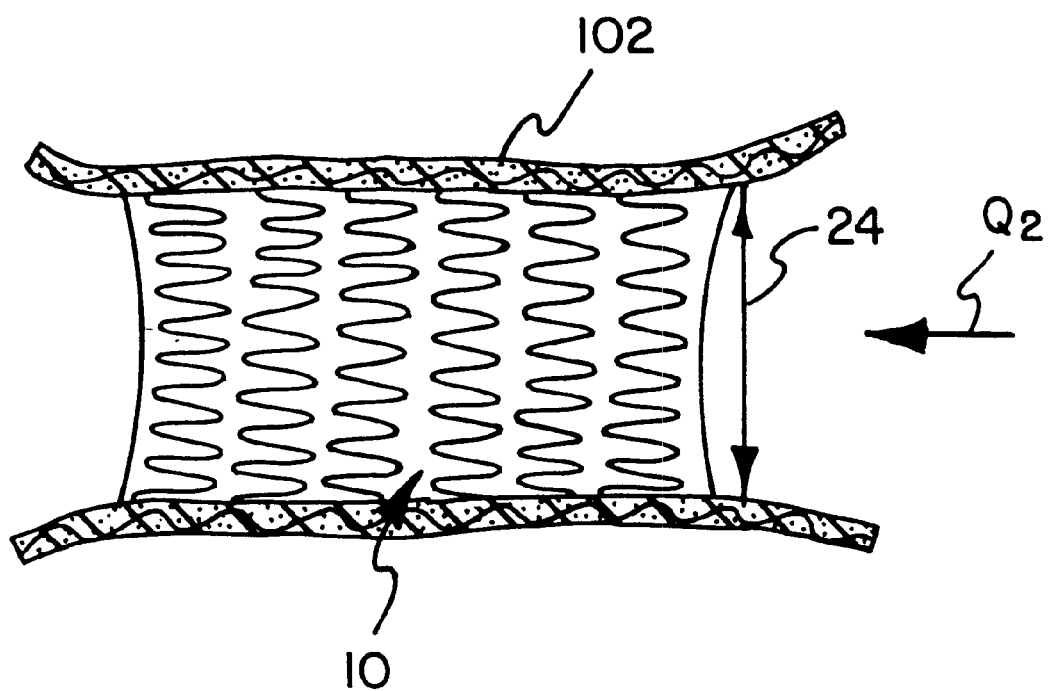
FIG. 18 is a cross-section view of the vessel of FIG. 20, with the stent-graft device having been dilated to a second functional diameter, thereby regulating the pressure and flow of fluid through the vessel.

FIGS. 17 and 18 show how flow through a conduit 102 can be adjusted using the device 10 of the present invention. The device 10 shown in FIG. 17 is at its second, self-expanded, dimension 18. At this dimension 18, flow of fluid through the device 10 can be represented as being at pressure $P_1$ and at a volume of flow $Q_1$. By dilating the device 10 to an enlarged third dimension 24 and assuming relatively constant hemodynamic conditions, as is shown in FIG. 18, the pressure through the conduit will decrease to a pressure $P_2$ and volume of flow will increase to a volume $Q_2$. By adjusting the extent of dilation between the second dimension 18 and the third dimension 24, a user can control flow rate and flow pressure through the conduit 102.

Figure 19:
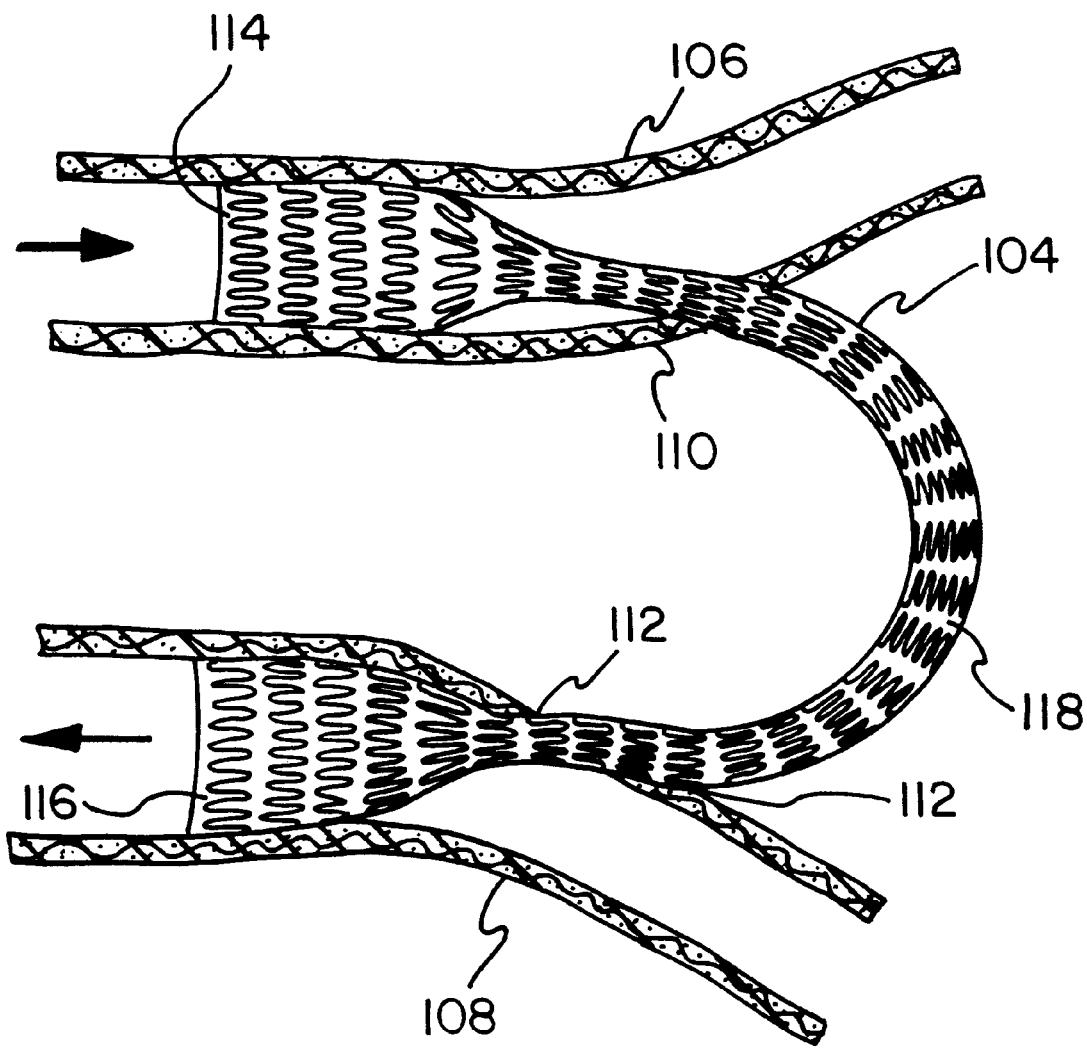
FIG. 19 is a cross-section view of a pair of vessels, having yet another embodiment of a stent-graft device of the present invention incorporated therein, the stent device serving as an extra-anatomic conduit with the ability to regulate flow between the two vessels.

FIG. 19 shows an example of how to employ a stent-graft device 104 of the present invention to perform a by-pass operation between two blood vessels 106, 108. In this instance the device 104 is constructed of sufficient length so as to be capable of being attached between the blood vessels 106, 108. Perforations 110, 112 are made in each of the blood vessels and a first end 114 of the device 104 is inserted into blood vessel 106 and a second end 116 of the device 104 is inserted into blood vessel 108. The device 104 will immediately self-expand to fill the perforations 110, 112 and its ends 114, 116 can then be dilated to form a snug fit within the blood vessels 106, 108, as is shown. It should be noted that a by-pass configuration can be implemented with the present invention to route flow around an obstruction in a single blood vessel.

The device 104 includes a center conduit segment 118 through which fluid flow is directed. This segment 118 may be constructed from conventional tubular material (for example, a tube formed from expanded polytetrafluoroethylene) or specially designed materials (for instance, it may be constructed from a self-sealing material that is particularly useful in dialysis treatments or in other applications requiring repeated access through the material with a needle or other device). In the embodiment illustrated, the center segment 118 comprises the same stent-graft material of the present invention previously described. Constructed from this material, the center segment can be dilated to form an improved fit within perforations 110, 112 and/or it can be dilated to control the flow rate or pressure through the device 104, as previously described.

Figure 20:
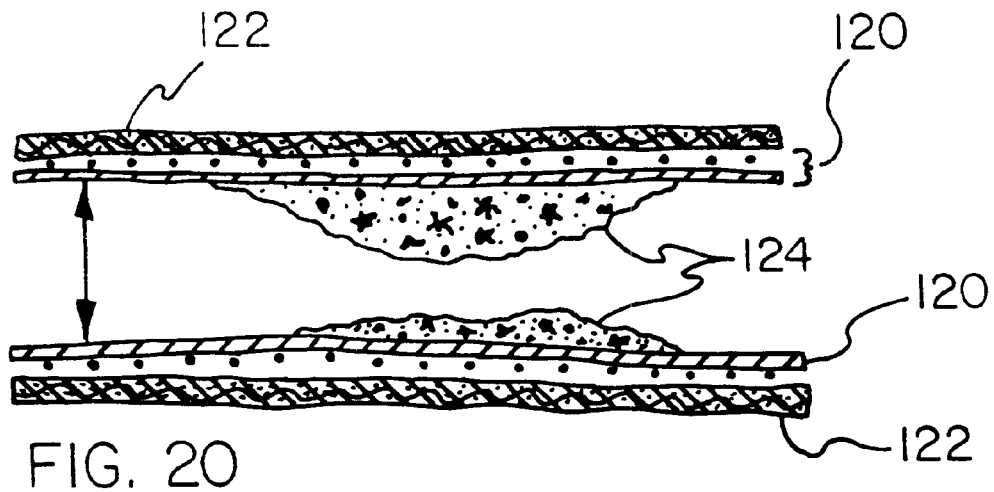
FIG. 20 is a cross-section view of a vessel containing a previous deployed stent-graft device of the present invention therein, a stenotic atherosclerotic lesion having formed within the stent-graft device.
Figure 21:
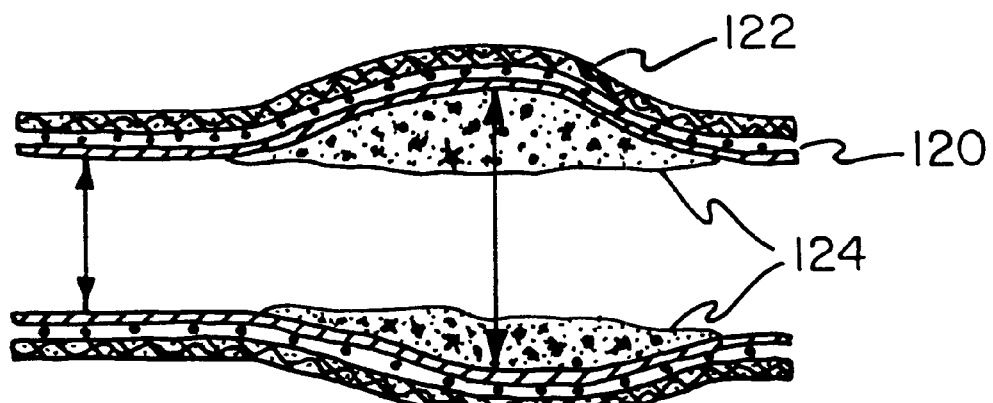
FIG. 21 is a cross-section view of the vessel of FIG. 20 illustrating revision of the restenotic lesion following balloon dilation to an ancillary diameter.
Figure 22:
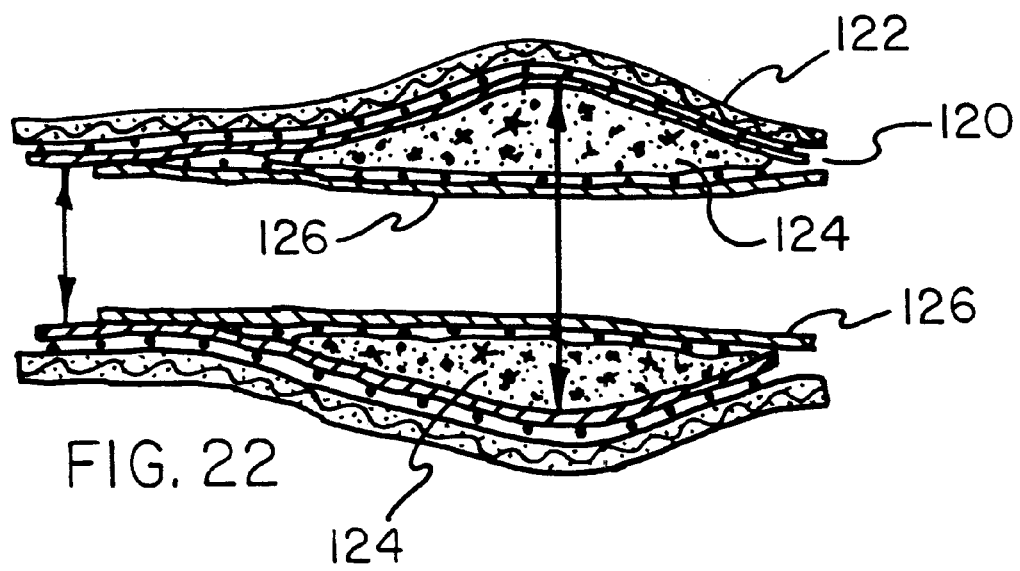
FIG. 22 is a cross-section view of the vessel of FIG. 21 wherein an adjunctive device is deployed to maintain patency through the revised lesion.

FIGS. 20 through 22 illustrate how the dilation properties of a device 120 of the present invention can be employed to correct a restenosis within a vessel 122. As is shown in FIG. 20, a stenotic atherosclerotic lesion 124 has formed on the interior of the stent-graft 120. The fact that the stent-graft 120 of the present invention can be balloon dilated allows the device 120 to be expanded in the manner shown in FIG. 21 to displace the lesion 124 out of the flow path through the vessel 122. This is possible due to the diametrical reserve capacity (i.e. the ability to selectively dilate the diameter of the device from one functional diameter to another) of the stent-graft 120. At this stage, an adjunctive stent-graft 126 can be employed over the stenosis to maintain the vessel 122 in an open position, as is shown in FIG. 22. The attribute of diametrical reserve is useful in the treatment of structures in the vessels of pediatric patients, such as aortic coarctation. Diametrical reserve, in this instance, allows the luminal diameter to be increased over time to account for growth of the recipient lumen.

Figure 23:
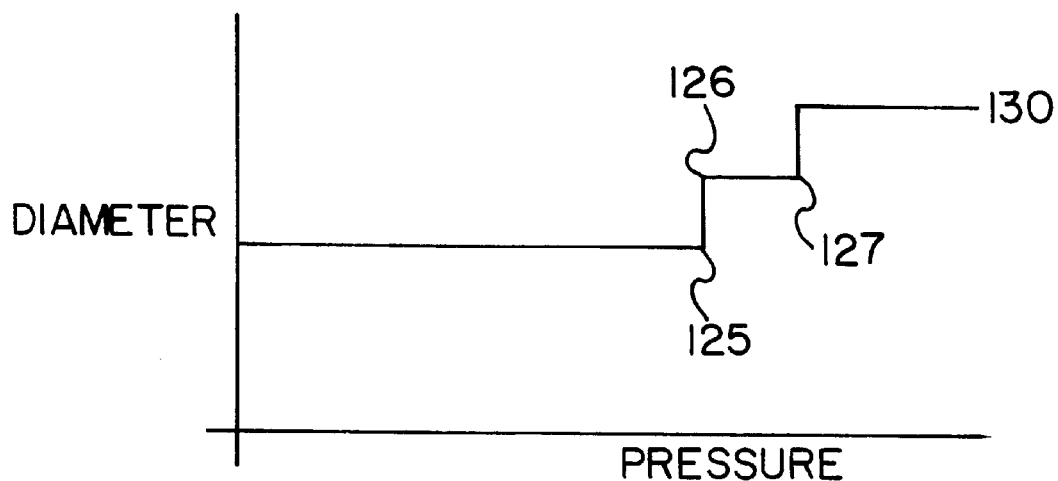
FIG. 23 depicts a pressure vs diameter curve for a device incorporating one or more sacrificial radial constraining elements.
Figure 24:
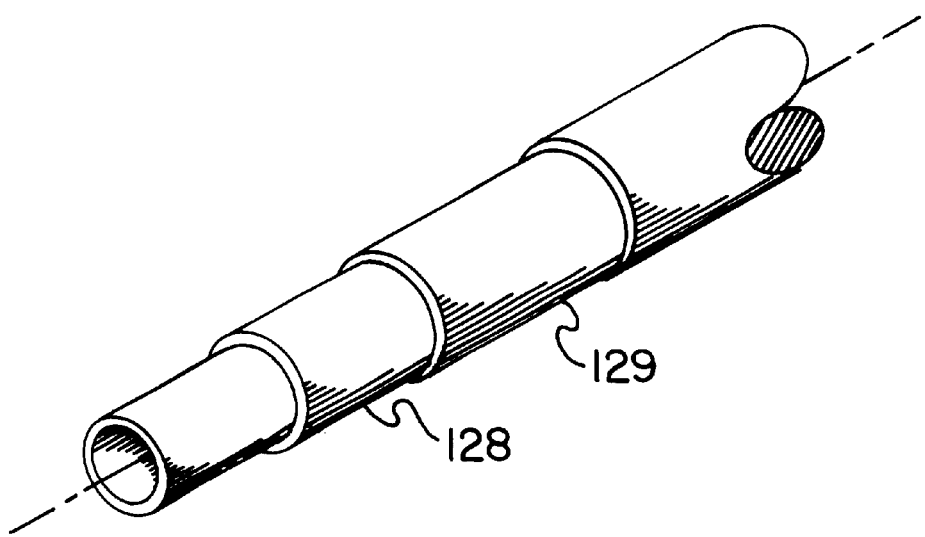
FIG. 24 is a three-quarter isometric view of a graft component of the present invention incorporating radially constraining elements.

One skilled in the art will readily appreciate that an alternative method of implementing the teachings of the present invention entails incorporation of multiple sacrificial radial constraints into the structure of the device. The sacrificial radial constraints may take the form of concentric tubular laminae incorporated into the wall of the tubular device wherein each successive tubular lamina has a different diameter, and will result in a pressure-diameter profile characterized by sequential diametrical steps as a function of pressure. This construction is shown in FIGS. 23 and 24. The device will maintain a first functional diameter over a range of intraluminal pressures below a first threshold pressure 125. The first threshold pressure is of sufficient magnitude to induce rupture or yielding of the sacrificial constraint lamina 128. When this radial constraint is disrupted, the diameter of the entire device will enlarge to an extent 126 defined by a successive radial constraint lamina 129. Further intraluminal pressurization can cause disruption of this second (or more) radial constraint lamina when its rupture or yield point is exceeded 127. This process may continue in kind until the device diameter achieves a maximal diameter 130.

Figure 25:
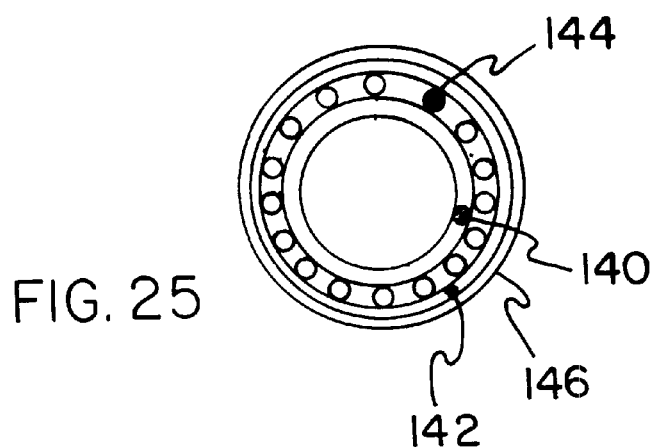
FIG. 25 is a cross-section view of another stent-graft device of the present invention.

FIG. 25 illustrates another configuration of a stent-graft of the present invention. The blood contacting conduit 140 may comprise an expanded PTFE seamless tube or an expanded PTFE film tube. The blood-contacting conduit 140 is attached to a stent 144, which, in turn, is covered, lined, or covered and lined by expanded PTFE laminae 142. This sub-assembly is covered by a constraining lamina 146, which may comprise an expanded PTFE seamless tube or an expanded PTFE film tube or combination tube/tubes and film/films. The function of the constraining lamina 146, alternatively, may be integral to tube 140 or tube 142.

Figure 26:
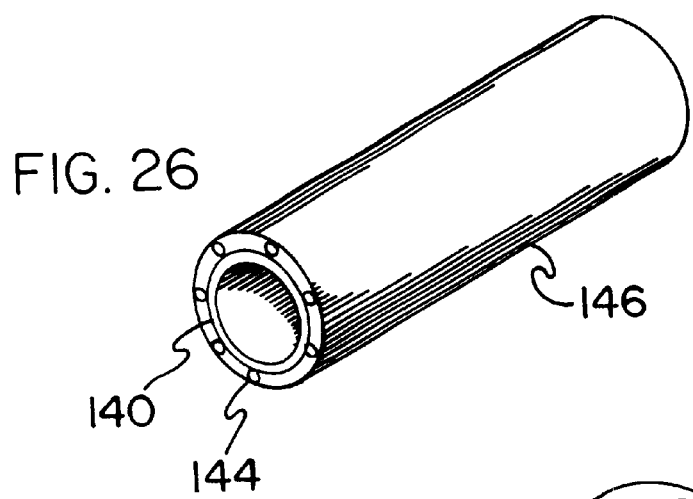
FIG. 26 is a three-quarter isometric view of the device of FIG. 25, shown in its introductory profile.

FIG. 26 shows a constraining lamina 146 completely covering the stent-graft, thereby completely covering stent 144.

Figure 27:
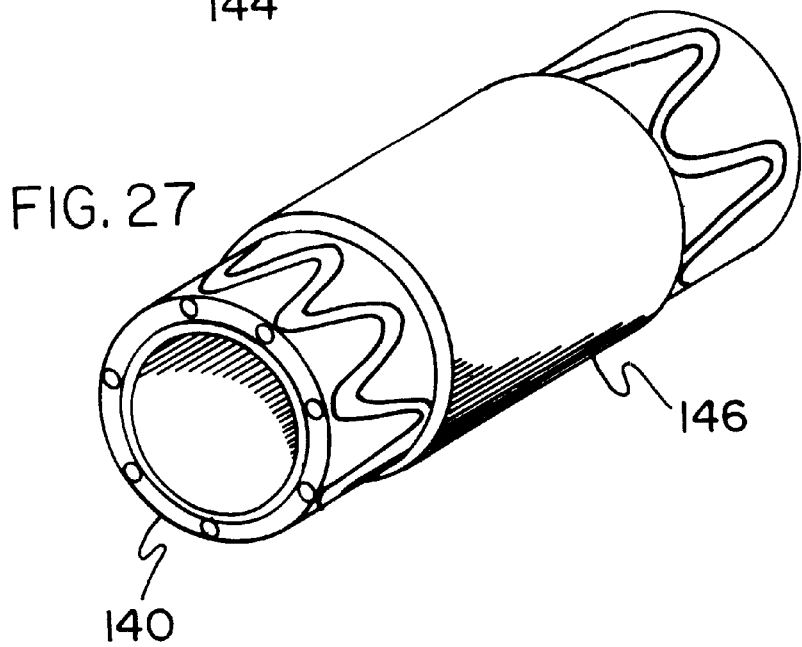
FIG. 27 is a three-quarter isometric view of the device of FIG. 25, shown after balloon dilation.

FIG. 27 shows that upon expansion, luminal surface 140 and abluminal surface 142 dilates, stent 144 dilates of its own accord since it is a self-expanding material, and constraining lamina 146 dilates and shortens in a controlled manner. This shortening insures that constraining lamina 146 is not exposed to the vessel lumen. Overall device length remains relatively constant (non-shortening).

The application of this device in a blood vessel is illustrated in FIGS. 28 through 32.

FIGS. 28A and 28B show a blood vessel 148 having a focal plaque 150. FIGS. 28A and 28B show that stent-graft 152 mounted over balloon catheter 154 can be placed across plaque 150 prior to deployment. FIGS. 30A and 30B show that when balloon 156 on catheter 154 is inflated, stent-graft 152 dilates and compresses plaque 150 against the vessel wall 148. FIGS. 31A and 31B show that after balloon catheter is deflated and removed, stent-graft 152 remains in place compressing plaque 150 against vessel wall 148.

Figure 32A:
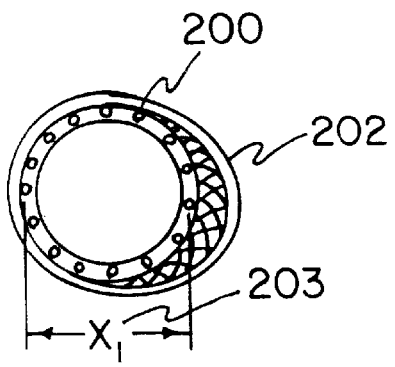
FIGS. 32A–32C are cross-section views of the device of the present invention undergoing compensatory enlargement within a vessel.
Figure 32B:
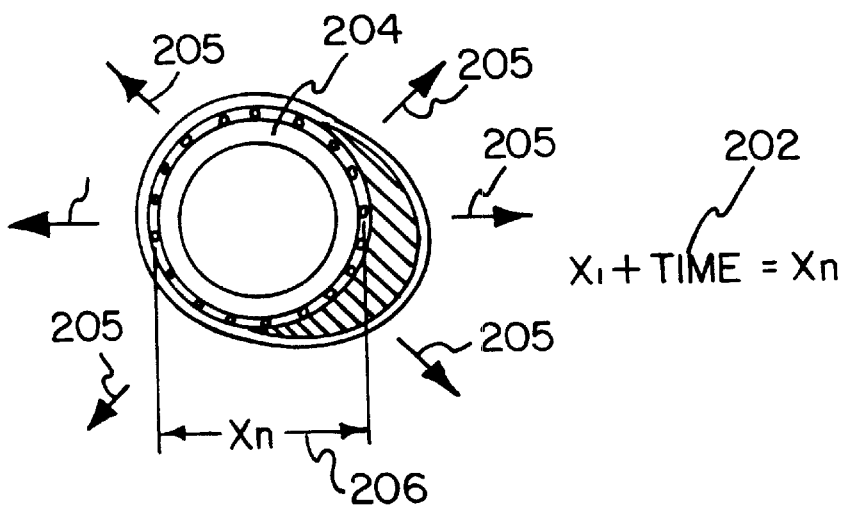
Figure 32C:
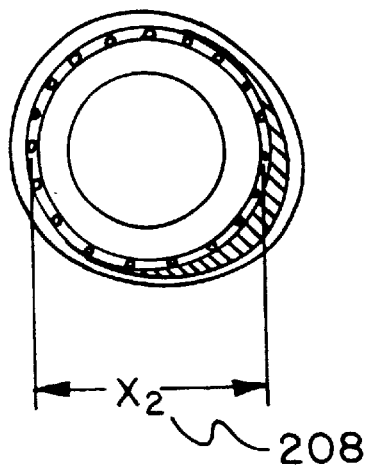

FIG. 32A pictorially depicts how the device of the present invention undergoes "compensatory enlargement." Stent-graft device 200 may be inserted and deployed within a lumen 202 at chosen endovascular therapy site to restore luminal patency. This occurs at the first functional diameter 203. As healing responses begin to compromise (that is, fill or partially occlude) the device lumen over time with tissue deposit 204, the self-expanding properties of the device cause it to "creep" outward in a radial or compensatory fashion (forces depicted by arrows 205). This outward creep may be symmetrical or asymmetrical, depending on the growth of the vessel. These creep forces in turn can cause the vessel itself to "remodel" to a larger size, thereby restoring or maintaining luminal patency. This is illustrated by growth to a larger diameter 206. These counteracting forces will continue over time until the device achieves its full functional diameter 208, at which point radial creep will cease.

Figure 33:
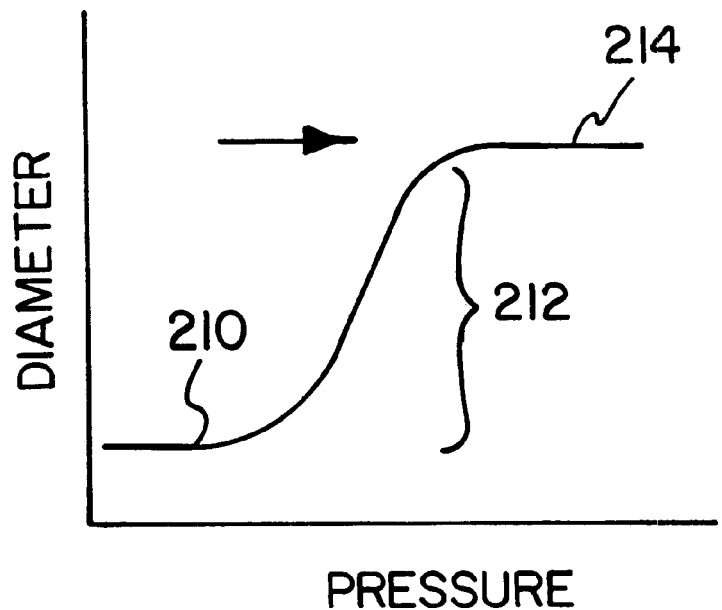
FIG. 33 is a graph showing the pressure/diameter results from a stentgraft constructed using an integral constraining lamina that dilates in a sigmoidal fashion with increasing pressure to a first operative diameter.
Figure 34:
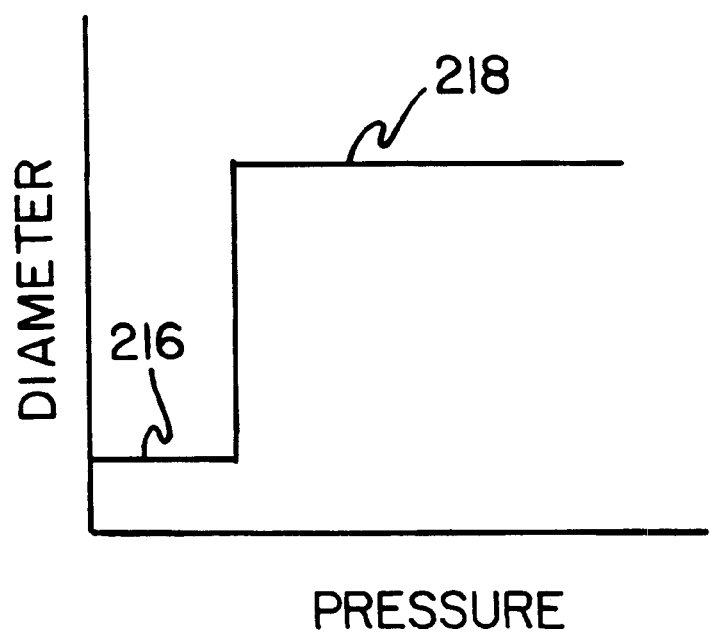
FIG. 34 is a graph showing the pressure/diameter results from a stent-graft constructed using an integral constraining lamina that disrupts at a given pressure allowing device to immediately expand to maximum diameter.

FIG. 33 shows the pressure/diameter results from a stent-graft constructed using a constraining lamina that dilates with increasing pressure in a sigmoidal fashion from a first diameter 210, through a range of possible intermediate diameters 212, to a fully enlarged diameter 214. FIG. 34 shows the pressure/diameter results from a stent-graft constructed using a constraining lamina that disrupts at a given pressure allowing device to immediately expand from a first diameter 216 to a second diameter 218.

Without intending to limit the scope of the present invention, the following examples illustrate how the present invention may be made and used:

EXAMPLE 1

Expanded PTFE tubes having 2.5 mm ID and a 0.13 mm (0.005 inch) wall thickness are employed. 100 cm lengths of these tubes are cut and carefully "sized-up" (i.e., enlarged through radially working) onto a 6 mm mandrel at room temperature. The entire tube is then longitudinally compressed to a length of 21–22 cm while mounted on the mandrel. The tubes are then placed in an oven and subjected to a thermal treatment of 370° C. for 5 minutes. After withdrawing from the oven and cooling, the tubes are carefully removed from the mandrel. The entire tube is then elongated (longitudinally) approx. 30%. The modified expanded PTFE base tube is then placed on a second 6 mm mandrel and dip-coated in an FEP dispersion Immediately upon removal from the dispersion, the tube is coated with FEP powder using a blender to atomize the powder. The FEP-coated tube is then placed in an oven and subjected to 300° C. for 10 minutes. Upon removal from the oven, and cooling of the mandrel, the modified expanded PTFE base tube is stripped from the mandrel in preparation for attachment to the stent-graft.

A 14 mm self-expanding nitinol stent frame, with anastomotic flares that externally support a 0.005 inch (0.01 cm) thick expanded PTFE tube, having 30 mm nominal fiber structure, is radially compressed by pulling it through a tapered die and capturing it in a glass tube having an ID of approx. 8 mm. A four piece radially expandable mandrel is covered with a 6 mm standard wall GORE-TEX® vascular graft used as a cushion tube (acquired from W.L. Gore & Associates, Inc., Flagstaff, Ariz.). The previously constructed modified expanded PTFE base tube as described above is slid over the cushion tube and the entire subassembly is inserted into the lumen of the glass capture tube and stent-graft subassembly. A pin is driven into the center of the mandrel to expand its outer diameter and to ensure a satisfactory interference fit between the modified base tube and the lining of the stent-graft. The entire assembly is then subjected to a temperature of 320° C. for 30 minutes to bond the balloon-distensible expanded PTFE tube to the inner surface of the stent-graft via FEP thermal adhesive.

This example produces a stent-graft having an initial inner diameter of about 7.5 mm, and, following dilatation, it expands from about 7.5 mm to about 14 mm.

EXAMPLE 2

Expanded PTFE materials typically exhibit anisotropic mechanical properties. Tensile strength in the direction of expansion, for example, is generally much greater than the tensile strength perpendicular to the direction of expansion. It is desirable that the mechanical strength of the expanded PTFE film/tape chosen for this device is greater in the longitudinal direction than the transverse direction. Consequently, when these materials are placed in longitudinal tension they are resistant to elongation. However, when subjected to transverse tension these materials have a propensity toward elongation in the transverse direction.

By applying a tensile force to a planar sheet of expanded PTFE at an angle with respect to the direction of expansion, an intermediate condition is reached in which there is a contribution of resistance to elongation and propensity for elongation. The actual deformation of the material becomes a force equilibrium problem that depends upon the underlying microstructure, material resin, and angle of application, i.e., relative contributions of longitudinal vs. transverse behavior. By varying the angle of force application with respect to the axis of expansion, one can manipulate the relative contributions inherent to the expanded PTFE material.

This behavior can be replicated by helically wrapping expanded PTFE film about an expanded PTFE base tube. In this manner, desirable aspects of both strength and distensibility in the radial direction can be achieved. The angle of the helix, relative to the long axis of the tube, can be altered determine the ratio of longitudinal vs. transverse tape/film lay and thus tailor the ratio of strength to distensibility in the radial direction.

Prototypes were made in accordance with this description in the following manner: The base tube is cut to 30 cm in length and loaded by hand onto a 90 cm long by 7.5 mm diameter mandrel. It is then positioned in a wrapper. The wrapper is capable of multiple passes at multiple angles. Using 1" (2.5 cm) wide film, 30° film payoff angle measured off of perpendicular to the mandrel, and two opposing passes produces a four film layer construction. After wrap, an identification number is applied and mandrel is removed from the wrapper and placed in an oven. The construction is heat treated for 4 minutes at 380° C. It is then removed from the oven and allowed to cool below 50° C. The composite is removed by hand from the mandrel.

A 14 mm self-expanding nitinol stent frame, with anastomotic flares that externally support a 0.005 inch thick (0.01 cm) expanded PTFE tube having 30 micron nominal fiber structure, is radially compressed by pulling it through a tapered die and capturing it in a glass tube having an ID of approx. 8 mm. A four piece radially expandable mandrel is covered with a 6 mm standard wall GORE-TEX® vascular graft used as a sacrificial cushion tube. The previously constructed modified expanded PTFE base tube as described above is slid over the cushion tube and the entire subassembly is inserted into the lumen of the glass capture tube and stent-graft subassembly. A pin is driven into the center of the mandrel to expand its outer diameter and to ensure a satisfactory interference fit between the modified base tube and the lining of the stent-graft. The entire assembly is then subjected to a heat treatment of 320° C. for 30 minutes to bond the balloon-distensible expanded PTFE tube to the inner surface of the stent-graft via FEP thermal adhesive.

This example produces a stent-graft having an initial inner diameter of about 7.5 mm, and, following dilatation, it expands from about 7.5 mm to about 14 mm.

EXAMPLE 3

A blood contacting conduit is formed from a longitudinally expanded PTFE film that is wrapped around a 0.0625" (0.16 cm) diameter solid stainless steel mandrel in an orientation perpendicular to the longitudinal axis of the film. The number of wraps is approximately 4 (with slight overlap). This sub-assembly is then helically over-wrapped with expanded PTFE film to compress the first expanded PTFE film wrap. The over-wrap is subsequently removed from the sub-assembly, and the compressed first expanded PTFE film wrap is constrained at the ends. This sub-assembly is then subjected to a thermal treatment of 370° C. for 5 minutes, air cooled, and stripped from the mandrel.

A 4.5 mm diameter nitinol stent is prepared for assembly by coating with fluorinated ethylene propylene (FEP) by dipping in dispersion (Neoflon ND-1X, available from Daikin located in Japan) and heat treating at 320° C. for 3 minutes.

The assembly process includes re-mounting the blood-contacting conduit on a 0.0625" (0.16 cm) diameter mandrel, radially compressing the FEP coated 4.5 mm diameter nitinol stent down to the outer diameter of the blood-contacting conduit (after thermally treating the nitinol with a refrigerant), helically wrapping the assembly with a polyimide film (such as KAPTON®, from E.I. duPont deNemours & Co.) and further helically wrapping with constraining wraps of an expanded PTFE film. This composite is then subjected to a thermal treatment of 320° C. for 5 minutes to adhere the FEP coated stent to the expanded PTFE blood-contacting conduit. The assembly is allowed to air cool, after which the device is stripped from the mandrel and trimmed as necessary.

EXAMPLE 4

In construction of a preferred embodiment, the stent structure is machined (by laser) from a nitinol tube and heat treated to achieve desired phase change characteristics and a surface oxide layer. This component is then powder coated with FEP. A 3.0 mm expanded PTFE base tube is loaded onto a 3.3 mm diameter mandrel and several layers of expanded PTFE/FEP film are wrapped transversely over the base tube. This mandrel is then heated to 320° C. for 5 minutes. The stent is then loaded over this film tube, aligned and pulled onto a 4 mm diameter mandrel. Several more transverse wraps of expanded PTFE/FEP film are applied over the stent and the assembly again heat treated at 320° C. for 5 minutes. After cooling, the expanded PTFE base tube is removed to leave a sub-assembly comprising a stent covered and lined with expanded PTFE film. FEP film is then applied by transversely wrapping with expanded PTFE/FEP film, FEP side out, to the outer surface of a base tube, which is loaded on a 2.75 mm diameter mandrel. This mandrel is then subjected to 370° C. for 8 minutes. The stent sub-assembly is then refrigerated and drawn down in radial size, through a tapered die onto the 2.75 mm diameter base tube and over wrapped with expanded PTFE film to maintain its smaller profile. This assembly is then heated to 320° C. for 2 minutes. After air cooling, the assembly is stripped off the mandrel. This assembly is again refrigerated and drawn down further in profile and captured in a constraining tube made from an expanded PTFE film. This constraining tube is produced by wrapping several layers of the expanded PTFE film onto a 0.062" (0.16 cm) diameter mandrel and heat treating for 4 minutes at 320° C. Once the stent-graft device is secured within the constraining tube (previously referred to as the "integral constraining lamina"), the device is trimmed to length. The device is constrained at the introductory profile until a distensive force is applied causing the stent-graft to expand either to the balloon diameter, or in the case of a sacrificial liner (refer below), to the profile of the vessel at which point it is restrained from further dilatation.

The outer constraint tube component may be made to yield at a given pressure, allowing the device to maintain its initial introductory profile until that given pressure is exceeded. Once the pressure is reduced below the threshold point, distention ceases. If the device has not been distended to its maximum diameter, further distention is possible by re-exceeding the pressure threshold. Similarly, the outer constraint tube component may be made to yield at a given pressure, allowing the device to maintain its initial introductory profile until that given pressure is exceeded. Once the pressure is reduced below the threshold point, rapid distention ceases, but the constant outward radial force imparted by the constrained stent may induce creep. If properly engineered, this creep will induce compensatory enlargement by slowly allowing the vessel to remodel. Still, if the device has not been distended to its maximum diameter, further distention is possible by re-exceeding the pressure. Similarly, the liner may be made of a distensible component laminated to a sacrificial component. Once the pressure threshold of the sacrificial layer has been exceeded, it yields and allows distention of the entire device. In this embodiment, the device will continue to expand (by force of the self-expanding stent component) until it is constrained by the vessel in which it was placed, or until it achieves its maximum diameter.

It is known that there are several different methods of radially compressing a self expanding nitinol stent in order to facilitate the bonding process. Among these include (but are not limited to): inducing a martensitic phase through the use of refrigerant; pulling the device through a tapered die; rolling; and radial crush through the use of devices such as iris diaphragms. Factors that may contribute to the decision of the method used include hoop strength and nitinol configuration used (e.g., tube, sheet, wire). Similarly, methods of constraining the stent in this condition during the adhesion cycle could include: wrapping with films, beads or fibers such as expanded PTFE and/or polyimide; or covering the assembly with a constraining tube. These methods are to provide examples only and not intended to limit the scope of the present invention.

Similarly there may be several ways in which the stent-graft can be manufactured. It is important to understand that it is not the manufacturing process that is crucial, but the inherent characteristics of the stent-graft. The examples provided are not intended to limit the scope of the invention, but to provide alternative manufacturing techniques. For instance, the stent may be attached through thermal adhesive to the distensible liner at its full functional diameter. After adhesion, the stent and liner/cover are refrigerated and pulled through a tapered die to an introductory/delivery profile. Through heat and tension, the device can be elongated, thereby radially shrinking the liner component providing a smooth, wrinkle-free luminal surface.

The nitinol stent component (which can be made from wire on a stent jig or laser cut from a tube of metal) is drawn down and adhered to the graft component. This adherence may be accomplished by heat with the use of thermoplastics or thermosetting materials, or by solvent liquified materials such as polyurethanes and the like. In some cases, the graft component may supply the radial strength necessary to constrain the self-expanding stent until a further distensive force is applied to it. This device retains the super elastic qualities of a self expanding stent, while allowing ease of delivery and deployment of a balloon adjustable stent.

With respect to certain definitions used herein, the "functional diameter" is the dimension in which the device is designed to function as clinical therapy in an interventional procedure. The present invention is intended to accommodate two or more functional diameters and may include an entire range of various dimensions depending on its distention properties. The term "maximum diameter" defines the largest dimension at which the device was designed for use. This diameter is usually the dimension at which the stent was heat treated and/or manufactured.

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:

1. An endoluminal prosthesis comprising
   a self-expanding stent element;
   a graft element comprising polytetrafluoroethylene attached to the stent element to form the endoluminal prosthesis;
   wherein the endoluminal prosthesis is constrained by a constraint to a first diametrical dimension for insertion into a lumen;
   wherein the endoluminal prosthesis self-expands to a second enlarged diametrical dimension when said constraint is removed, the endoluminal prosthesis being restricted from further diametrical enlargement by the graft element; and
   wherein the graft element yields under applied distensive force to enlarge at least a portion of the endoluminal prosthesis to a third diametrical dimension at least 10% larger than the second diametrical dimension, the endoluminal prosthesis maintaining the third diametrical dimension when the distensive force is removed; and
   wherein the stent element undergoes longitudinal shortening of less than 15% when enlarged from the first diametrical dimension to the third diametrical dimension.

2. The endoluminal prosthesis of claim 1 wherein the stent element provides the expansive force to achieve the second dimension.

3. The endoluminal prosthesis of claim 2 wherein the graft element is distensible to a third dimension upon application of a distensive force in excess of that exerted by the stent element.

4. The endoluminal prosthesis of claim 1 wherein the stent element provides at least a portion of the distensive force to achieve the third dimension.

5. The endoluminal prosthesis of claim 1 wherein the graft element comprises an expanded polytetrafluoroethylene.

6. The endoluminal prosthesis of claim 1 wherein the graft element undergoes deformation between the second and third dimensions.

7. The endoluminal prosthesis of claim 1 wherein the graft element undergoes deformation between the first and second dimensions.

8. The endoluminal prosthesis of claim 1 wherein the prosthesis is adapted to be expanded beyond its second dimension with a distensive force of an expandable balloon.

9. The endoluminal prosthesis of claim 1 wherein the prosthesis is capable of further expansion beyond the third dimension upon application of further distensive force thereto.

10. The endoluminal prosthesis of claim 1 wherein the prosthesis is capable of selective diametrical distention beyond the second dimension.

11. The endoluminal prosthesis of claim 1 wherein
    the device has a fluid-flow lumen therethrough; and
    the diameter of the lumen is adjustable beyond the second dimension to regulate flow through the lumen.

12. The endoluminal prosthesis of claim 1 wherein the prosthesis is adapted to be inserted into a body lumen and selectively diametrically expanded to prevent leakage of fluid around the device.

13. The endoluminal prosthesis of claim 1 wherein the prosthesis is adapted to be inserted into a body structure and selectively diametrically expanded to establish at least one intraluminal anastomosis.

14. The endoluminal prosthesis of claim 1 wherein the prosthesis is adapted to be inserted into a body structure and diametrically expanded to compensate for changes in the surrounding vasculature over time.

15. The endoluminal prosthesis of claim 1 wherein the prosthesis has smooth continuous internal surface therethrough, regardless of diameter, beyond the second dimension.

16. The endoluminal prosthesis of claim 1 wherein the prosthesis has smooth continuous internal surface therethrough, regardless of diameter beyond the first dimension.

17. The endoluminal prosthesis of claim 1 wherein
    the prosthesis has a longitudinal length; and
    the prosthesis distends from the second diametrical dimension to the third diametrical dimension with substantially no shortening along the length of the prosthesis.

18. The endoluminal prosthesis of claim 1 wherein
    the prosthesis includes at least a first and a second region; and
    the prosthesis includes different expansive properties between the first and the second regions.

19. The endoluminal prosthesis device of claim 1 wherein the prosthesis is resistant to expansion at initial installation between the second and the third dimensions until a minimum threshold distensive force is applied thereto.

20. The endoluminal prosthesis of claim 1 wherein the device is adapted to be inserted into a body structure and expanded in place to achieve and maintain a taper along its length.

21. The endoluminal prosthesis of claim 1 wherein once distended to a third diametrical dimension the prosthesis is resistant to recoil or further distention until a threshold pressure is reached.

22. The endoluminal prosthesis of claim 1 wherein the second dimension is at least 50% larger than the first dimension.

23. The endoluminal prosthesis of claim 1 wherein the second dimension is at least 75% larger than the first dimension.

24. The endoluminal prosthesis of claim 1 wherein the second dimension is at least 100% larger than the first dimension.

25. The endoluminal prosthesis of claim 1 wherein the third dimension is at least 30% larger than the second dimension.

26. The endoluminal prosthesis of claim 1 wherein the third dimension is at least 50% larger than the second dimension.

27. The endoluminal prosthesis of claim 1 wherein the third dimension is at least 75% larger than the second dimension.

28. The endoluminal prosthesis of claim 1 wherein the third dimension is at least 100% larger than the second dimension.

29. The endoluminal prosthesis of claim 1 wherein the prosthesis longitudinally shortens no more than 10%.

30. The endoluminal prosthesis of claim 1 wherein the prosthesis longitudinally shortens no more than 7%.

31. The endoluminal prosthesis of claim 1 wherein the prosthesis longitudinally shortens no more than 5%.

32. The endoluminal prosthesis of claim 1 wherein graft element has a relatively smooth continuous internal surface over a range of operative diameters.

33. The endoluminal prosthesis of claim 1
wherein the stent element exerts a continuous outward radial force after initial installation so as to allow the prosthesis to enlarge further over time.

34. The endoluminai prosthesis of claim 1
wherein the by a constraint is resistant to the stent element; and wherein after experiencing a threshold pressure, the constraint allows the stent element to self-expand.

35. The endoluminal prosthesis of claim 1 in which the stent element is constrained through the constraint external to the device.

36. The endoluminal prosthesis of claim 35 in wherein enlargement beyond the first diametrical dimension occurs when the constraint is removed.

37. The endoluminal prosthesis of claim 1 in which the stent element is constrained through the constraint integral to the device.

38. The endoluminal prosthesis of claim 37 in which deformation of the constraint allows diametrical enlargement beyond the first diameter.

39. The endoluminal prosthesis of claim 38 wherein deformation of the constraint is achieved via distensive force.

40. The endoluminal prosthesis of claim 38 in which disruption of the constraint allows enlargement beyond the first diameter.

41. The endoluminal prosthesis of claim 40 wherein disruption of the constraint is achieved via distensive force.

* * * * *